US010183273B2

(12) United States Patent
Scavone et al.

(10) Patent No.: US 10,183,273 B2
(45) Date of Patent: *Jan. 22, 2019

(54) ABSORBENT ARTICLE COMPRISING CYCLODEXTRIN COMPLEXES

(71) Applicant: The Procter & Gamble Company, Cincinnati, OH (US)

(72) Inventors: Timothy Alan Scavone, Loveland, OH (US); James Steven Riedeman, Cincinnati, OH (US); Victor Nicholas Vega, Cincinnati, OH (US); Dean Larry DuVal, Lebanon, OH (US); Mike P. Purdon, Hebron, KY (US); Peter Christopher Ellingson, Symmes Township, OH (US); Ebrahim Rezai, Mason, OH (US); Vince Scott Stapp, Florence, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/630,976

(22) Filed: Jun. 23, 2017

(65) Prior Publication Data

US 2017/0368532 A1 Dec. 28, 2017

Related U.S. Application Data

(60) Provisional application No. 62/354,306, filed on Jun. 24, 2016.

(51) Int. Cl.
| | | |
|---|---|---|
| *B01J 20/24* | (2006.01) | |
| *A61L 15/28* | (2006.01) | |
| *A61L 15/46* | (2006.01) | |
| *B01J 20/32* | (2006.01) | |
| *A61F 13/49* | (2006.01) | |
| *A61L 9/01* | (2006.01) | |
| *C11B 9/00* | (2006.01) | |

(52) U.S. Cl.
CPC ......... *B01J 20/24* (2013.01); *A61F 13/49007* (2013.01); *A61L 9/01* (2013.01); *A61L 15/28* (2013.01); *A61L 15/46* (2013.01); *B01J 20/3231* (2013.01); *C11B 9/0061* (2013.01); *A61F 13/49* (2013.01); *A61L 2300/802* (2013.01)

(58) Field of Classification Search
CPC ....... B01J 20/24; B01J 20/3231; A61L 15/28; A61L 15/46
USPC ...................................................... 502/404
See application file for complete search history.

(56) References Cited

U.S. PATENT DOCUMENTS

| | | |
|---|---|---|
| 3,654,929 A | 4/1972 | Nilsson et al. |
| 4,460,364 A | 7/1984 | Chen |
| 4,589,876 A | 5/1986 | Van Tilburg |
| 4,608,047 A | 8/1986 | Mattingly |
| 4,687,478 A | 8/1987 | Van Tillburg |
| 5,304,161 A | 4/1994 | Noel et al. |
| 5,342,333 A | 8/1994 | Tanzer et al. |
| 5,591,146 A | 1/1997 | Hasse |
| 5,733,272 A | 3/1998 | Brunner et al. |
| 5,769,832 A | 6/1998 | Hasse |
| 5,769,833 A | 6/1998 | Hasse |
| 5,951,534 A | 9/1999 | Cummings et al. |
| 6,110,449 A | 8/2000 | Bacon et al. |
| 6,488,947 B1 | 12/2002 | Bekele |
| 6,613,703 B1 * | 9/2003 | Yahiaoui ............ A61K 8/0208 428/305.5 |
| 6,653,521 B1 | 11/2003 | Kurata et al. |
| 7,163,529 B2 | 1/2007 | Mocadlo |
| 7,473,817 B1 | 1/2009 | Tanaka et al. |
| 8,558,051 B2 | 10/2013 | Toshishige et al. |
| 8,686,215 B2 | 4/2014 | Caputi et al. |
| 9,592,168 B2 | 3/2017 | Caputi et al. |
| 9,731,042 B2 | 8/2017 | Scavone et al. |
| 2002/0011584 A1 | 1/2002 | Uchiyama et al. |
| 2004/0122386 A1 | 6/2004 | Mocadlo |
| 2004/0147416 A1 | 7/2004 | Woo et al. |
| 2005/0053784 A1 * | 3/2005 | Wood ..................... A61L 15/28 428/372 |
| 2005/0089540 A1 | 4/2005 | Uchiyama et al. |
| 2006/0129118 A1 | 6/2006 | Mocadlo |
| 2006/0165622 A1 | 7/2006 | Hiramoto et al. |
| 2008/0033381 A1 | 2/2008 | Albino et al. |
| 2008/0071238 A1 | 3/2008 | Sierri et al. |
| 2008/0085290 A1 | 4/2008 | Flugge-Berendes et al. |
| 2008/0215023 A1 | 9/2008 | Scavone et al. |
| 2010/0076389 A1 | 3/2010 | Burrow et al. |
| 2010/0287710 A1 | 11/2010 | Denutte et al. |
| 2010/0324512 A1 | 12/2010 | Caputi et al. |
| 2011/0152146 A1 | 6/2011 | Denutte et al. |
| 2011/0152804 A1 | 6/2011 | Woo et al. |
| 2012/0107258 A1 | 5/2012 | Kuhn et al. |

(Continued)

FOREIGN PATENT DOCUMENTS

| | | |
|---|---|---|
| WO | WO1998026808 A2 | 6/1998 |
| WO | WO2007011058 A1 | 1/2007 |

OTHER PUBLICATIONS 10-undecenal, SCIFINDER Database (online), American Chemical Society, 2016 (retrieved on Feb. 15, 2016), retrieved from the internet: <URL:https://scifinder.cas.org?, p. 1.

(Continued)

*Primary Examiner* — Edward M Johnson
(74) *Attorney, Agent, or Firm* — George H. Leal

(57) ABSTRACT

Absorbent articles having a cyclodextrin complex of one or more odor controlling organic compounds wherein the cyclodextrin is a substituted cyclodextrin (wherein the H atom of OH groups in positions 2, 3 and 6 is partially or entirely replaced by a substituent —R) having a substitution degree (DS) of 0.4 or more —R substituents per molecule of cyclodextrin and wherein substitution in position 2 is 20% or above, in position 6 is 20% or above and in position 3 is 50% or below. Cyclodextrin complexes of this type release the odor controlling organic compound much faster and in more complete manner than non-substituted or differently substituted cyclodextrin complexes thus the odor control efficacy is improved.

16 Claims, 5 Drawing Sheets

(56) References Cited

U.S. PATENT DOCUMENTS

| | | |
|---|---|---|
| 2012/0157805 A1 | 6/2012 | Caputi et al. |
| 2012/0157946 A1 | 6/2012 | Caputi et al. |
| 2012/0226248 A1 | 9/2012 | Caputi et al. |
| 2013/0090390 A1 | 4/2013 | Singer et al. |
| 2013/0158490 A1 | 6/2013 | Caputi et al. |
| 2013/0158491 A1 | 6/2013 | Caputi et al. |
| 2014/0377207 A1 | 12/2014 | Scavone et al. |
| 2014/0378920 A1 | 12/2014 | Scavone et al. |
| 2014/0378921 A1 | 12/2014 | Scavone et al. |
| 2015/0044309 A1 | 2/2015 | Davies |
| 2016/0175214 A1 | 6/2016 | Scavone et al. |

OTHER PUBLICATIONS

International Search Report and Written Opinion for PCT/US2017/038988 dated Sep. 28, 2017.
Liquid Definition, Collins English Dictionary, Harper Collins Publishers 2014.

* cited by examiner

Figure 4

ABSORBENT ARTICLE COMPRISING CYCLODEXTRIN COMPLEXES

FIELD OF THE INVENTION

The present invention relates to an absorbent article comprising cyclodextrin complexes of odor controlling organic compounds, wherein the cyclodextrin is a substituted cyclodextrin.

BACKGROUND OF THE INVENTION

Absorbent articles, according to the present invention, are articles which can be used to absorb any type of fluid. These articles include absorbent hygienic articles (like for example sanitary napkins, pantyliners, tampons, inter labial articles, adult incontinence articles such as adult incontinence pads, pants and diapers, baby pants and diapers, breast pads and hemorrhoid pads). Other absorbent articles, according to the present invention, can be for example absorbent paper towels, wipes, toilet paper, or facial tissues as well as absorbent articles used in the medical field such as wound dressings and surgical articles and absorbent articles used in food technology and conservation (such as fluid pads for meat, fish and so on). Absorbent articles, according to the present invention, encompass also absorbent materials used industrially to absorb fluids (for example, to contain spillage of chemicals in fluid form).

Absorbent hygienic articles are commonly used to absorb, and in some cases, retain bodily fluids and other exudates excreted by the human or animal body, such as urine, menses, blood, fecal materials or mucus or chemicals or any type of fluid waste. Paper towels, wipes, facial tissues, toilet paper, and other absorbent articles may be used also to absorb kitchen and food residues and/or any kind of dirt or waste. In many cases, the absorbed materials can be malodorants or can generate malodors with time while the article is still being used, or after it has been disposed of or thrown in the trash.

Materials for controlling and reducing malodors in absorbent articles have been identified in the art. Odor absorbers (such as activated carbon, zeolites, silica and the like) have been widely used to trap volatile malodorant molecules in porous solids. Also, uncomplexed cyclodextrin molecules have been used to trap malodorant molecules by complexing them, and thus reducing their volatility therefore acting similarly to odor absorbers.

However, the action of odor absorbers is not always satisfactory, so that in the art they have been complemented or replaced by odor controlling organic compounds which play an active role in reducing the perception of malodors. Among these odor controlling organic compounds, fragrances (i.e. chemicals or blends of chemicals which stimulate the olfactory receptors providing a pleasant smell), odor masking compounds (i.e. compounds which stimulate the olfactory receptors so that unpleasant odors are perceived less or perceived as less disturbing), and reactive compounds (i.e. compounds which chemically react with the malodorant molecules altering their nature) are known and have been described e.g. in patent applications published under number EP1886698, EP2114331 EP2468308 EP3010555 EP3010554 EP3010553, all assigned to the Procter & Gamble Company.

It is also known from the art cited above, that these odor controlling organic compounds can be introduced into the absorbent articles in the form of complexes with cyclodextrin. This is beneficial in some cases, because fragrances and odor masking compounds are, by definition, volatile materials and therefore tend to evaporate from the absorbent articles during storage and use, thus losing efficacy. Most reactive compounds are also volatile, so the formation of cyclodextrin complexes prevents their evaporation as well. Moreover, all reactive compounds (volatile and less volatile) being "reactive", they tend to have poor chemical stability. The formation of cyclodextrin complexes also protects the reactive molecules from unwanted reactions, greatly improving their chemical stability during storage and usage of the absorbent articles.

When odor controlling organic compounds are incorporated into absorbent articles in the form of cyclodextrin complexes, they are typically released from the cyclodextrin complexes when the article comes into contact with the fluids to be absorbed. This is typically the moment at which malodors can start developing and at which the release of odor controlling compounds is more necessary. This has also been described in the documents cited above.

Known cyclodextrin complexes are relatively effective in releasing the complexed odor controlling organic compounds, however, an aspect where an improvement can still be beneficial is improving the kinetics and the completeness of the release. As mentioned above, the need for controlling malodors typically occurs at the exact moment when a fluid is absorbed into the article (e.g. urine or menstrual fluids in hygienic articles, blood from food preparation absorbed by a paper towel and so on). Current cyclodextrin complexes, although very efficient, still require a certain amount of time to release the odor controlling compounds, and therefore in some cases, it is possible that malodors can be perceived (even if only for a short time) between the moment the fluid is absorbed and the moment when the odor controlling compounds are released.

The perception of menstrual or urine malodor when wearing an absorbent article is clearly unwanted, even if only for a short time, and it can cause embarrassment and loss of personal confidence. There is also a high demand for technologies which counteract malodors in the fastest possible way in the kitchen and among medical uses.

Based on the foregoing, what is needed is an absorbent article which utilizes an improved odor control composition, facilitated application of odor control composition, and/or improved placement of the odor control composition within the absorbent article.

SUMMARY OF THE INVENTION

The present invention relates to absorbent articles comprising a cyclodextrin complex of one or more odor controlling organic compounds, wherein said cyclodextrin is a substituted cyclodextrin (wherein the H atom of OH groups in positions 2, 3 and 6 is partially or entirely replaced by a substituent —R) having a substitution degree (DS) of 0.4 or more —R substituents per molecule of cyclodextrin and wherein substitution in position 2 is 20% or above, in position 6 is 20% or above and in position 3 is 50% or below.

The present invention also encompasses a method to manufacture an absorbent article the method comprising:
  providing a solution in a solvent system said solution comprising a substituted cyclodextrin as described above and an odor controlling organic compound,
  applying an amount of the solution to one of the layers making up the absorbent article and preferably evaporating the solvent so to precipitate the cyclodextrin complex.

BRIEF DESCRIPTION OF THE DRAWINGS

FIG. 4 is a graph depicting the GC-MS signal peak areas of perfume materials emanating from dry versus wetted AGM, which possesses MBCD coated on the AGM surface or incorporated within the AGM particle

DETAILED DESCRIPTION OF THE INVENTION

Figure 1:
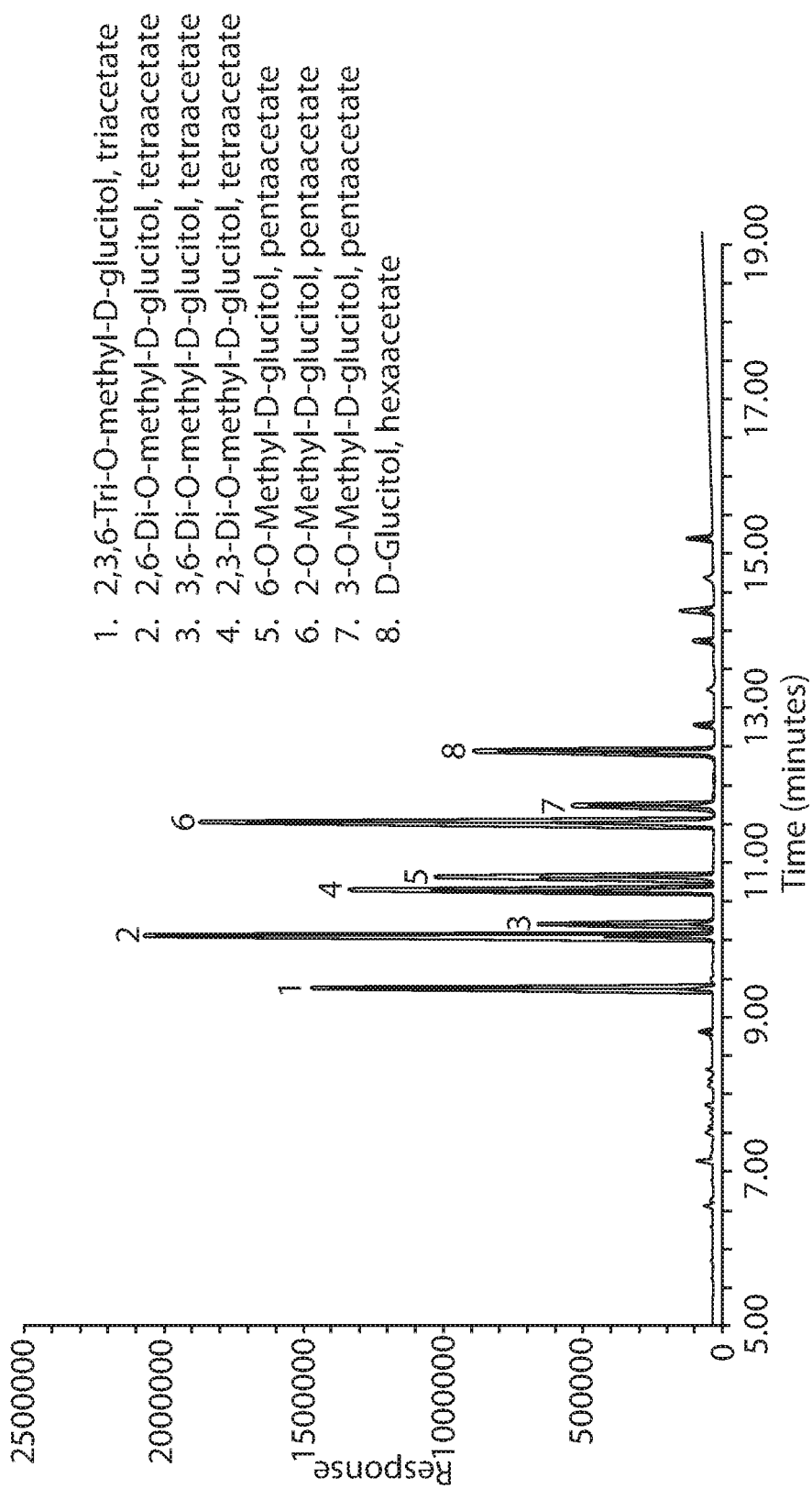
FIG. 1 is a graph depicting a representative chromatogram of hydrolyzed, reduced, and acetylated methyl β-cyclodextrin.

The present invention pertains to cyclodextrin complexes comprising position-specific-substituted cyclodextrins comprising one or more odor controlling compounds, hereafter, "substituted cyclodextrin complexes." The position-specific-substituted cyclodextrins described herein comprises various degrees of substitution in the 2, 3, and 6 positions. As discussed herein, position-specific-substituted cyclodextrins with substitution in positions 2 and 6 provide benefits over conventional β-cyclodextrins and over completely substituted cyclodextrins, i.e. substitution in positions, 2, 3, and 6. There are many benefits to utilizing position-specific-substituted cyclodextrins. For example, position-specific-substituted cyclodextrins have a higher solubility than their conventional β-cyclodextrin counterparts. The increased solubility can provide more rapid release of encapsulated fragrances in the position-specific-substituted cyclodextrin. Also, with the increased solubility, less moisture may be required to liberate encapsulated fragrances in the position-specific-substituted cyclodextrin. This increased solubility can also mean that less position-specific-substituted cyclodextrin may be utilized in absorbent articles than their β-cyclodextrin counterparts.

Because of the increased solubility of the position-specific-substituted cyclodextrins, there are methods of application of the position-specific-substituted cyclodextrins which are not available for their conventional β-cyclodextrin counterparts. With the new methods of application, the position-specific-substituted cyclodextrins may be provided to areas of the absorbent article which may not have been possible with their conventional β-cyclodextrin counterparts. Additionally, the position-specific-substituted cyclodextrins can provide higher efficacy than their conventional β-cyclodextrin counterparts.

The aforementioned benefits of utilizing position-specific-substituted cyclodextrins are discussed in additional detail herein.

"Absorbent article" refers to articles that absorb any type of fluid. These articles are typically disposable and include paper towels, wipes, toilet paper, facial tissue, absorbent articles used in the medical field such as wound dressings and surgical articles, absorbent articles used in food technology and conservation (such as fluid pads for meat, fish and the like), absorbent articles used industrially to absorb fluids, for example to contain spillage of chemicals in fluid form and absorbent hygienic articles. The term "absorbent hygienic articles" refers to devices that absorb and contain body exudates, such as urine, menses, blood and feces. The term "disposable" is used herein to describe absorbent articles which are not intended to be laundered or otherwise restored or reused as an absorbent article after a single use. Examples of absorbent hygienic articles include diapers, toddler training pants, adult incontinence pants, pads or diapers, and feminine hygiene garments such as sanitary napkins, pantiliners, tampons, interlabial articles, breast pads, hemorrhoid pads, and the like.

Absorbent hygienic articles and components thereof, including a topsheet, backsheet, absorbent core, and any individual layers of these components, can have a body-facing surface and a garment-facing surface. As used herein, "body-facing surface" means that surface of the article or component which is intended to be worn toward or adjacent to the body of the wearer, while the "garment-facing surface" is on the opposite side and is intended to be worn toward or placed adjacent to the wearer's undergarments when the disposable absorbent article is worn.

Most absorbent hygienic articles of the present invention (except those for internal use such as tampons) typically comprise a topsheet, a backsheet, and an absorbent core disposed between the topsheet and backsheet.

Absorbent articles of the present disclosure may utilize improved odor control compositions, facilitated application of odor control compositions, and/or improved placement of the odor control compositions within the absorbent article. For example, it has been surprisingly found that by selecting the cyclodextrin molecule forming the complex with the odor controlling organic compounds from position-specific-substituted cyclodextrin (wherein the H of some OH groups is replaced by a substituent —R) having a substitution degrees of 0.4 or more —R groups per glucose unit and wherein substitution in position 2 is 20% or above, in position 6 is 20% or above and in position 3 is less than the substitution percentage of position 2 and/or position 6, the kinetic and the completeness of the release are significantly improved. Additional benefits of utilizing position-specific-substituted cyclodextrins are discussed in additional detail herein.

Topsheet

The topsheet of the absorbent hygienic article is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), polymeric materials such as apertured formed thermoplastic films, apertured plastic films, and hydroformed thermoplastic films, porous foams, reticulated foams, reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

In some forms, the topsheet may be a laminate of two or more materials, e.g. including a nonwoven and a film. In such forms, the nonwoven may form a body-facing surface of the topsheet. Or, the film may form at least a portion of the body-facing surface of the topsheet. Films for use as topsheets are discussed in U.S. Pat. Nos. 4,629,643; 5,460, 623; and 6,563,013. Additional examples of formed films suitable for use as a topsheet or a portion thereof are described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986.

Nonlimiting examples of woven and nonwoven materials suitable for use as the topsheet or a portion thereof include fibrous materials made from natural fibers, modified natural fibers, synthetic fibers, or combinations thereof. These fibrous materials can be either hydrophilic or hydrophobic, but it is preferable that the topsheet be hydrophobic or rendered hydrophobic. Some suitable nonwoven materials suitable for use as a topsheet are described in U.S. Pat. Nos. 5,792,404 and 5,665,452.

Backsheet

The backsheet can be impervious to liquids (e.g., menses and/or urine) and can be preferably manufactured from a thin plastic film, although other flexible materials may also be used such as nonwovens. As used herein, the term "flexible" refers to materials which are compliant and will readily conform to the general shape and contours of the human body. The backsheet can prevent the exudates absorbed and contained in the absorbent core from wetting articles which contact the absorbent article such as bedsheets, pants, pajamas and undergarments. The backsheet can also be vapor permeable ("breathable"), while remaining fluid impermeable. The backsheet may comprise a woven or nonwoven material, polymeric films such as thermoplastic films of polyethylene or polypropylene, or composite materials such as a film-coated nonwoven material.

The backsheet can comprise panty fastening means applied on its surface, particularly the surface facing outside the absorbent article in order to allow the article to stay in place when worn between the user's crotch and panties. Such panty fastening means can be for example a layer of adhesive or mechanical means such as Velcro® or combination thereof. When an adhesive is present, typically a release paper is also present in order to protect the adhesive before use.

The backsheet and the topsheet can be positioned respectively adjacent the garment surface and the body surface of the absorbent core. The absorbent core can be joined with the topsheet, the backsheet, or both in any manner as is known by attachment means, such as those well known in the art. Embodiments of the present invention are envisioned wherein portions of the entire absorbent core are unattached to either the topsheet, the backsheet, or both.

Absorbent Core

The absorbent core can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers. Other suitable absorbent core materials include absorbent foams such as polyurethane foams or high internal phase emulsion ("HIPE") foams. Suitable HIPE foams are disclosed in U.S. Pat. No. 5,550,167, U.S. Pat. No. 5,387,207, U.S. Pat. No. 5,352,711, and U.S. Pat. No. 5,331,015. Other suitable materials for use in absorbent cores comprise open celled foams or pieces thereof. The use of foams in absorbent cores is described in additional detail in U.S. Pat. Nos. 6,410,820; 6,107,356; 6,204,298; 6,207,724; 6,444,716; 8,211,078, and 8,702,668.

In some forms, the absorbent core structure may comprise a heterogeneous mass layer or may utilize methods or parameters such as those described in U.S. patent application Ser. No. 14/715,984, filed May 19, 2015; U.S. patent application Ser. No. 14/750,399, Jun. 25, 2015; U.S. patent application Ser. No. 14/751,969 filed Jun. 26, 2015; U.S. patent application Ser. No. 15/078,132 filed Mar. 23, 2016; U.S. patent application Ser. No. 14/750,596 filed Jun. 25, 2015; U.S. patent application Ser. No. 15/084,902 filed Mar. 30, 2016; U.S. patent application Ser. No. 15/343,989 filed Nov. 4, 2016; U.S. patent application Ser. No. 15/344,273 filed Nov. 4, 2016; U.S. patent application Ser. No. 15/344,294 filed Nov. 4, 2016; U.S. patent application Ser. No. 14/704,110 filed May 5, 2015; U.S. patent application Ser. No. 15/194,894 filed Jun. 28, 2016; U.S. patent application Ser. No. 15/344,050 filed Nov. 4, 2016; U.S. patent application Ser. No. 15/344,117 filed Nov. 4, 2016; U.S. patent application Ser. No. 15/344,177 filed Nov. 4, 2016; U.S. patent application Ser. No. 15/344,198 filed Nov. 4, 2016; U.S. patent application Ser. No. 15/344,221 filed Nov. 4, 2016; U.S. patent application Ser. No. 15/344,239 filed Nov. 4, 2016; U.S. patent application Ser. No. 15/344,255 filed Nov. 4, 2016; U.S. patent application Ser. No. 15/464,733 filed Nov. 4, 2016; U.S. Provisional Patent Application No. 62/437,208 filed Dec. 21, 2016; U.S. Provisional Patent Application No. 62/437,225 filed Dec. 21, 2016; U.S. Provisional Patent Application No. 62/437,241 filed Dec. 21, 2016; or U.S. Provisional Patent Application No. 62/437,259 filed Dec. 21, 2016. The heterogeneous mass layer has a depth, a width, and a height.

In some forms, a combination of absorbent core materials may be utilized. For example, forms are contemplated where a first layer of an absorbent core comprises a foam material or pieces thereof as described previously, and a second layer of an absorbent core comprises an airlaid material. Such combinations are described in U.S. Patent Publication No. 2014/0336606 and U.S. Pat. No. 9,649,228.

For some absorbent articles, the absorbent core can be relatively thin, less than about 5 mm in thickness, or less than about 3 mm, or less than about 1 mm in thickness. Thickness can be determined by measuring the thickness at the midpoint along the longitudinal centerline of the pad by any means known in the art while under a uniform pressure of 1.72 kPa.

The absorbent core can comprise superabsorbent materials such as absorbent gelling materials (AGM), including AGM fibers, as is known in the art. The absorbent core can therefore constitute a layer comprising superabsorbent material.

The absorbent article can comprise other additional components, for example between the topsheet and absorbent core, such as a secondary topsheet or acquisition layer. The secondary topsheet or acquisition layer can comprise a tissue layer or a nonwoven, such as carded resin-bonded nonwovens, embossed carded resin-bonded nonwovens, high-loft carded resin-bonded nonwovens, carded through-air bonded nonwovens, carded thermo-bonded nonwovens, spun-bonded nonwovens, and the like. A variety of fibers can be used in the secondary topsheet or acquisition layer, including natural fibers, e.g. wood pulp, cotton, wool, and the like, as well as biodegradeable fibers, such as polylactic acid fibers, and synthetic fibers such as polyolefins (e.g., polyethylene and polypropylene), polyesters, polyamides, synthetic cellulosics (e.g., RAYON®, Lyocell), cellulose acetate, bicomponent fibers, and blends thereof. The basis weight of the secondary topsheet or acquisition layer can vary depending upon the desired application. In some forms, the secondary topsheet or acquisition layer may comprise a super absorbent polymer, e.g. AGM deposited thereon. In such forms, the secondary topsheet or acquisition layer may comprise a first AGM while the absorbent core comprises a second AGM. In some forms, the first AGM may be different than the second AGM.

The absorbent article can comprise further components such as side cuffs, typically found in diapers, or side wings or side flaps, typically found in sanitary napkins.

Absorbent catamenial tampons are absorbent articles for internal use in the vagina which are typically made by a pledget comprising absorbent fibers compressed to a cylindrical shape. Tampons can be "digital tampons" when they have a self-sustaining shape and can be inserted with a finger or "applicator tampons" i.e. tampons which are introduced using an applicator. Tampons can also comprise an extraction cord so to facilitate extraction from the vagina.

Absorbent hygienic articles herein are often commercialized in packages containing a plurality of units, often the package is a plastic film or a carton box. Single units contained within the commercial package can be individually packaged or not.

Additional Layers

In some forms, the absorbent articles of the present disclosure may comprise additional layers disposed between the topsheet and the absorbent core and/or between the absorbent core and the backsheet. Some examples include a secondary topsheet, acquisition layer, and/or distribution layer which can be disclosed between the topsheet and the absorbent core. Other examples include distribution layers or liquid-impermeable layers which are disposed between the absorbent core and the backsheet.

Structure of Substituted Cyclodextrin Complex

For "complex", it is intended to mean an "inclusion complex" within the meaning of IUPAC Compendium of Chemical Terminology 2nd Edition (1997), wherein the complexing agent (the cyclodextrin in this case) is the host and the complexed compound is the "guest".

As known, cyclodextrins are a family of compounds where a number of glucose units are bound together in a ring shaped structure (cyclic oligosaccharides). More specifically cyclodextrins are formed by 5 or more α-D-glucopyranoside units connected through the glycosidic linkages in positions 1 and 4 on the glucose ring. Typically, the number of glucose units forming each ring is from 6 to 12 and the most common forms are those with 6, 7 or 8 glucose units also called alpha-cyclodextrin, beta-cyclodextrin, gamma-cyclodextrin respectively.

In all cyclodextrins, each glucose units has three OH groups bound to the carbon atoms in positions 2, 3 and 6. As mentioned previously, the inventors have surprisingly found that the utilization of position-specific-substituted cyclodextrins provides benefits over their β-cyclodextrin and completely substituted counterparts.

As used herein, the term "position-specific-substituted cyclodextrin" includes any cyclodextrin wherein one or more hydrogen atom of the OH groups in positions 2 and 6 of the glucose units is replaced by a substituent —R thus forming an —OR group. Similarly, as used herein, the term "completely substituted cyclodextrin" includes any cyclodextrin wherein each of the OH groups in positions 2, 3, and 6 have been replaced by OR groups. The average number of —R substituents for each glucose unit in a given sample represents the "degree of substitution" (DS) which is a number ranging from 0 to 3 where 0 corresponds to no substitutions (all OH groups in position 2, 3 and 6 are present) and 3 to a complete substitution (all OH groups in position 2, 3 and 6 are replaced by OR groups). The average is calculated on a molar basis.

The absorbent articles of the present invention comprise substituted cyclodextrin complexes of one or more odor controlling organic compound, wherein the substituted cyclodextrin complex comprises position-specific-substituted cyclodextrins. The substituted cyclodextrin complex has a substitution degree (DS) of 0.4 or more —R substituents per molecule of cyclodextrin and wherein substitution in position 2 is 20% or above, in position 6 is 20% or above.

In some forms of the invention, the average degree of substitution can be between 0.4 and 2.5, between 0.9 and 2.4, between 1.2 and 2.2, between 1.6 and 2.1, specifically reciting all values within these ranges and any ranges created thereby. In some forms of the invention, the substitution in position 2 can be between 20 and 90%, more preferably between 45% and 80%. In some forms of the invention, the substitution in position 6 can be between 20 and 90%, more preferably between 45% and 80%. In some forms, the invention may encompass combinations of the preferred aspects mentioned above.

It is worth noting that position-specific-substituted cyclodextrins are synthesized from conventional cyclodextrins. Via this synthesis, a variety of cyclodextrin molecules are created. For example, some of the cyclodextrin molecules may not be substituted at all, i.e. all OH groups in positions 2, 3, and 6 are present. As another example, some of the cyclodextrin molecules will be substituted as desired, i.e. position-specific-substituted cyclodextrins. And, as another example, some of the cyclodextrins will experience complete substitution, i.e. all OH groups are substituted in positions 2, 3, and 6 by OR groups. However, as discussed herein, the position-specific-substituted cyclodextrins, with substitution in positions 2 and 6, provides additional benefits over the completely substituted cyclodextrins. As such, forms of the present invention are contemplated where the degree of substitution in position 3 is less than the level of substitution in position 2 and/or position 6. In some forms, the degree of substitution in position 3 is less than about 50 percent, less than about 40 percent, less than about 30 percent, less than about 20 percent, or less than about 10 percent, specifically reciting all values within these ranges and any ranges created thereby.

The —R substituents in the —OR groups can be selected from any substituent having a carbon atom in position 1 (thus forming an —O—C— bond with the oxygen atom). Suitable —R substituents may include carbon atoms chains which are saturated or unsaturated and can be straight or branched. For example, suitable —R substituents include saturated and straight chain C1-6 alkyl, hydroxyalkyl, and mixtures thereof. Particularly suitable —R substituents have a carbon chain of from 1 to 6 carbon atoms and are selected from alkyl, hydroxyalkyl, dihydroxyalkyl, carboxy-alkyl, aryl, maltosyl, allyl, benzyl, alkanoyl, and mixtures thereof, wherein the term "alkyl" encompasses both linear and branched alkyl chains.

In some forms, an —R substituent may comprise propyl, ethyl, methyl, and hydroxypropyl. Different —R substituents can be present in the same position-specific-substituted cyclodextrin sample on the same cyclodextrin molecule and even on the same cyclodextrin glucose unit.

In one particular form, all the —R substituents may be methyl substituents. In this case, the cyclodextrin is also called "methylated β-cyclodextrin". For example, a particularly suitable cyclodextrin material for the present invention is a methylated cyclodextrin having a DS of 0.4 or higher, preferably from 0.4 to 2.5, more preferably between 0.9 and 2, even more preferably between 1.2 and 1.8 and wherein at least 20%, preferably between 20% and 90%, more preferably between 45% and 80% of the —OH groups in positions 2 and 6, respectively, are methylated.

The degree of substitution can be measured with gas chromatography as described below, with reference to methyl substituents in β-Cyclodextrin.

It has been surprisingly found that substituted cyclodextrin complexes, according to the present invention, release more rapidly the odor controlling organic compound when the absorbent article is contacted with an aqueous fluid, compared with similar complexes wherein the cyclodextrin does not comprise position-specific-substituted cyclodextrins or where the substitution is distributed between positions 2, 3 and 6.

In general, cyclodextrin complexes, including substituted cyclodextrin complexes, can help prevent the evaporation of the complexed fragrance compounds. In use, moisture from urine or menses contacts the cyclodextrin complex and dissolves the crystalline structure of the cyclodextrin complex. This causes the release of the fragrance materials within the cyclodextrin complex. However, a problem exists when incorporating a cyclodextrin complex in an absorbent hygienic article. Other components, such as the absorbent core and/or superabsorbent material, of the absorbent article have a strong affinity for bodily fluids, e.g. menses and urine, including the moisture contained therein. So, when an absorbent article is insulted with bodily fluid, such as menses or urine, the cyclodextrin complex can be in competition with the absorbent core and/or superabsorbent material for the moisture contained in the bodily fluid. The absorbent core and/or superabsorbent material has a strong affinity for the moisture and once the absorbent core and/or superabsorbent material contacts the bodily fluid, the absorbent core and/or superabsorbent material effectively "lock-up" the moisture of the bodily fluid, thereby reducing the amount of moisture available to contact the cyclodextrin complex. So, only a limited amount of moisture may be available to dissolve the cyclodextrin crystalline structure and release the fragrance compounds to provide odor control benefits.

With conventional cyclodextrin complexes, a larger amount of moisture may be required to solubilize the cyclodextrin molecules and release the encapsulated fragrance. The same holds true for completely substituted cyclodextrins where positions 2, 3, and 6 are substituted. However, the inventors have surprisingly found that with the use of a position-specific-substituted cyclodextrins, as described herein, less moisture may be required to solubilize the position-specific-substituted cyclodextrins. So, more of the complexed fragrance compounds may be released without compromising the absorbent or retention capacity of the absorbent article.

Determination of Methyl Substituent Distribution

The Methyl Substituent Distribution in Methylated β-Cyclodextrin (hereafter "MBCD") is measured using gas chromatograph with split/splitless injection and flame ionization detection (a suitable instrument is the Agilent 7890B GC available from Agilent, Santa Clara, Calif., or equivalent). The β-cyclodextrin is hydrolyzed, reduced and then acetylated for analysis. Additionally, gas chromatography/mass spectrometry (a suitable unit is the 5777A Mass Selective Detector (MSD) also available from Agilent, or equivalent) can be used to identify the acetylated products to confirm peak identity. Both instruments are calibrated and operated as per the manufacturer's instructions.

Derivatization reagents must be used with a purity of greater than or equal to 99%, except for the borohydride (98%), and can be obtained from Sigma Aldrich, or equivalent. Fifty mg of MBCD and 5 mL of 2 M trifluoroacetic acid solution were added to a 50 mL round bottom flask with magnetic stir bar. The reaction vessel was fitted with a water cooled condenser and heated to reflux for 4 hours while stirring. After complete hydrolysis, the reaction mixture was evaporated under vacuum to dryness. Next, the hydrolysis product, 10 mL of ammonium hydroxide (32% in water), and 101 mg sodium borohydride (2.67 mmols) were stirred in a 50 mL round bottom flask at 40° C. for 2 hours. Residual sodium borohydride was quenched via dropwise addition of glacial acetic acid until the solution pH was in the range of 4.5 to 6. The resulting boric acid was removed via sequential additions of methanol (4×20 mL) to the reaction mixture, followed by evaporation under vacuum at 40° C. The reaction product, 10 mL of pyridine, 36 mg of 4-dimethylaminopyridine (0.2947 mmols), and 630 µL acetic anhydride (630 µL, 6.6794 mmols) were added to a 50 mL round bottom flask with magnetic stir bar. The reaction was stirred vigorously at room temperature for 20 hours. The acetylated alditol products were extracted with 10 mL chloroform using a 60 mL separatory funnel and washed three times with 10 mL of deionized water. The chloroform extract was diluted (1:3) with chloroform, and sampled for gas chromatography analysis.

The GC analysis was performed on a 30 m long by 0.250 mm inner diameter column with 5% phenyl arylene methylpolysiloxane phase at a 1 µm film thickness (a suitable column is the DBSMS available from Agilent, or equivalent USP G27 phase). The GC inlet was set at 280° C. in Split mode (5:1 split, glass wool packed liner) with a 3 mL septum purge. A 1.5 mL/minute column flow of helium was set at an oven temperature of 150° C. under constant flow conditions. The detector was set at 300° C. with flows set to the instrument manufacturer's recommended conditions. The GC oven was programmed to begin at 150° C. for 1 min, then ramp at 15° C./min to 250° C., hold for 4 min at 250° C., then ramp at 10° C./min to 315° C. and a final hold of 1 min. 1 µL of the chloroform extract is injected for analysis. A representative chromatogram of MBCD (CAVASOL® W7 M from Wacker Chemie AG) is given in FIG. 1. It is understood that one skilled in the art can slightly modify the chromatographic conditions to achieve the necessary separation as needed.

GC-MS analysis is performed under the same chromatographic conditions as for the flame ionization detection (FID). The temperature for the MSD transfer line and detector were set to 280° C. and 300° C. respectively. The MSD was configured for electron ionization at −70 eV scanning from 35 m/z to 400 m/z with a scan rate of 257 msec/scan. The Total Ion Chromatogram was evaluated using the fragmentation data in Table 1 to assign retention order of the glucitol products. The retention order was then applied to the GC-FID chromatograms.

For quantification, each peak measured by GC-FID that is associated with a glucitol monomer is integrated to give a peak area. The areas are then used in Equations 1 and 2 to calculate the mole percent (mol %) of each glucitol monomer and reported to the nearest 0.1 mol %. The results from the example chromatogram in FIG. 1 are given in Table 1.

$$\text{mols glucitol } A = \text{mg } \beta \text{ cyclodextrin} \times \quad \text{Eq. 1}$$

$$\frac{\text{FID area counts for glucitol } A}{\sum \text{FID area counts of all glucitol monomers}} \times \frac{1}{MW_A}$$

where $MW_A$ is the molecular weight of the acetylated glucitol and mg β-cyclodextrin is the starting mass of underivatized MBCD.

$$\text{mol \% glucitol } A = \frac{\text{mols glucitol } A}{\sum \text{mols of all glucitol monomers}} \times 100\% \quad \text{Eq. 2}$$

Additionally, the mol % of particular substitutions are calculated by addition of the individual mol %. For example, mol % of all glucitols methylated at the 6 position (denoted in Table 1 as X6) would be the sum of the mol % of S2,6, S3,6 and S2,3,6.

The average degree of substitution was calculated according to Equation 3. Mol % for all glucitol monomers sharing the same number of methyl substituents (0, 1, 2, or, 3) were summed, multiplied by their respective methyl substituent number (0, 1, 2, or 3) and divided by 100. The result is reported to the nearest 0.1 mol %.

$$DS \text{ per glucose unit} = \frac{1}{100} \sum_{i=0}^{3} i \cdot \text{mol } \% \, x \quad \text{Eq. 3}$$

Where mol % x is equal to the summation of glucitol monomers having same number of methyl groups.

Data from a gas chromatogram of acetylated D-glucitol derivatives prepared from MBCD using the procedure described above is provided in Table 1. Table 1 shows Selected Fragments of Ionized D-Glucitol Acetates while FIG. 1 is an FID trace.

TABLE 2

| Substituent Distribution | mol % |
|---|---|
| Unsubstituted | 9.1 |
| S2 | 21.9 |
| S3 | 5.8 |
| S6 | 10.4 |
| S2, 3 | 13.7 |
| S2, 6 | 20.1 |
| S3, 6 | 6.1 |
| S2, 3, 6 | 12.8 |
| X6 | 49.5 |
| X2 | 68.6 |
| X3 | 38.5 |
| Avg. DS per Glusose Unit: | 1.6 |

The position-specific-substituted cyclodextrins of the present invention can be prepared by using methods known in the art for the selective modifications of cyclodextrins. For example, by using methods described by Khan et al. (Chem. Rev. 1998, 98, 1977-1996). Alternative synthesis routes for the preparation of the position-specific-substituted cyclodextrins of the invention are known to the chemists skilled in the field and broadly described in literature. For example, U.S. Pat. No. 5,710,268 and the textbooks "Advances in cyclodextrin chemistry" by Werz, Vidal, Guiou, Sollogoub, Matthieu, Wiley-VCH Verlag GmbH ed. 2014; and "Modern Synthetic Methods in Carbohydrate Chemistry: From Monosaccharides to Complex Glycoconjugates", Werz, Daniel B.; Vidal, Sebastian, eds, 2014 Wiley-VHC Verlag GmbH provide additional details.

Once the position-specific-substituted cyclodextrins is provided, substituted cyclodextrin complexes of odor controlling organic compounds which are active against malodors can be prepared as known in the art for the known cyclodextrin complexes, for example using the kneading method described in U.S. Pat. No. 5,571,782 and U.S. Pat. No. 5,543,157 or, using the spray drying method described in WO2008/104690A2.

Substituted Cyclodextrin Complex Positioning

The substituted cyclodextrin complex of the present invention can be disposed in various locations in the absorbent article. In all cases, the substituted cyclodextrin com-

TABLE 1

| | m/z | | | | | | | | | | | | | | | |
|---|---|---|---|---|---|---|---|---|---|---|---|---|---|---|---|---|
| Compound | 99 | 113 | 117 | 129 | 145 | 157 | 159 | 161 | 189 | 217 | 231 | 233 | 261 | 289 | 305 | 333 |
| 2,3,6-Tri-O-methyl-D-glucitol, 1,4,5-triacetate | X | X | X | X | | | X | | | | | X | | | | |
| 2,6-Di-O-methyl-D-glucitol, 1,3,4,5-tetraacetate | | | X | X | | | X | | | | X | | | X | | |
| 3,6-Di-O-methyl-D-glucitol, 1,2,4,5-tetraacetate | X | X | | X | | X | X | | X | | | X | | | | |
| 2,3-Di-O-methyl-D-glucitol, 1,4,5,6-tetraacetate | X | | X | | | | X | X | | | X | | X | | X | |
| 6-O-methyl-D-glucitol, 1,2,3,4,5-pentaacetate | X | | | X | X | X | X | | | X | X | | | X | | X |
| 2-O-methyl-D-glucitol, 1,3,4,5,6-pentaacetate | | | X | X | | X | X | | | | X | | | | | X |
| 3-O-methyl-D-glucitol, 1,2,4,5,6-pentaacetate | X | | | X | X | | X | | X | X | X | | X | | | |
| D-glucitol hexaacetate | | | | | X | X | | | | | X | | | X | | |

X = Fragment present in mass spectra

Table 2 provides data of the substituent distribution for MBCD, the average degree of methylation of the O6 and O2 positions, and the average degree of substitution (DS) per glucose unit.

plex can be simply applied on a surface of the article using any application method. More specifically, in the case of paper towels, wipes, toilet paper and facial tissues, the substituted cyclodextrin complex can be applied on any surface of any of the layers making up the article or be mixed with the fibers during the making process.

In the case of absorbent hygienic articles, the substituted cyclodextrin complex can be disposed on the garment-facing side or the body-facing side of the topsheet or absorbent core, or on the body-facing side of the backsheet. In some forms, the substituted cyclodextrin complex is disposed on the absorbent core. In such forms, the substituted cyclodextrin complex may be disposed on the body-facing side of the absorbent core. The substituted cyclodextrin complex can also be disposed on other components of the absorbent article, when present, such as the garment-facing side or body-facing side of a secondary topsheet or acquisition layer. The substituted cyclodextrin complex can also be mixed with any of the fibers or materials making up any of the layers of the absorbent article.

In some forms, the substituted cyclodextrin complex of the present invention is disposed in the absorbent article in or on a layer that is closer to the body-facing surface of the absorbent article than the absorbent core or a layer comprising superabsorbent material (e.g. absorbent gelling material ("AGM")). In general, the substituted cyclodextrin complex needs to come into contact with moisture to effectively release the compound.

Surprisingly, it has been discovered that if the substituted cyclodextrin complex is coated onto the outside surface of the AGM particle, that this can actually speed activation and release of the complexed fragrance compounds. Without being bound by theory, it is believed that the high solubility of the complexes of the present invention and the relatively slow kinetic absorption by the AGM particles allow the complete dissolution of the complexes before the AGM granule is able to compete for the liquid absorption. And, it is believed that the location of the substituted cyclodextrin complex on the surface of the AGM granule provides for a complete release exactly when and where it may be needed i.e. where a possible malodorant liquid is present. This can result in a more effective release of the complexed odor controlling organic compounds and can provide for improved odor control benefits.

Examples were created and tested with regard to efficacy of the substituted cyclodextrin complex of the present disclosure in various locations of an absorbent article. Data is provided with regard to the graph of FIG. 3. Components of the absorbent article tested were topsheet, acquisition layer (AQL), core cover, and AGM surface. As shown, the executions of substituted cyclodextrin complexes disposed on the topsheet and on the AGM surface were more effective than substituted cyclodextrin complexes in the AQL and the core cover. These examples are discussed in additional detail in the Test Procedures section herein.

Figure 3:
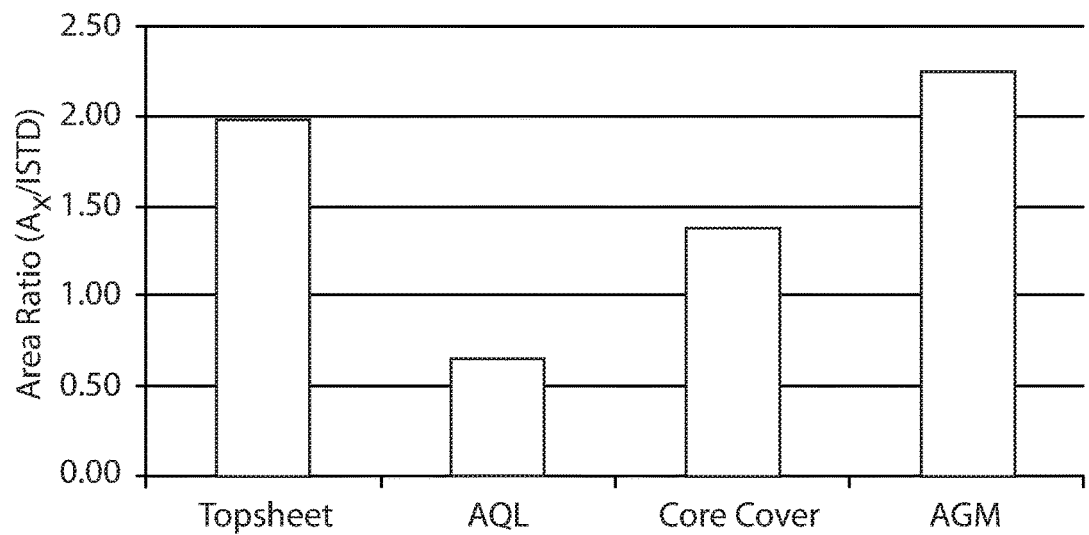
FIG. 3 is a chart depicting the total perfume release from MBCD coated onto various components of a diaper.

Based on FIG. 3, forms of the present invention are contemplated where a substituted cyclodextrin complex is applied to an absorbent article such that the substituted cyclodextrin complex provides a peak area ratio of greater than about at least 1.0. In another form, a substituted cyclodextrin complex can be provided to an absorbent article such that the substituted cyclodextrin complex provides a peak area ratio of greater than about 1.5, greater than about 1.75, or greater than about 2.0, specifically reciting all values within these ranges and any ranges created thereby.

Figure 4:
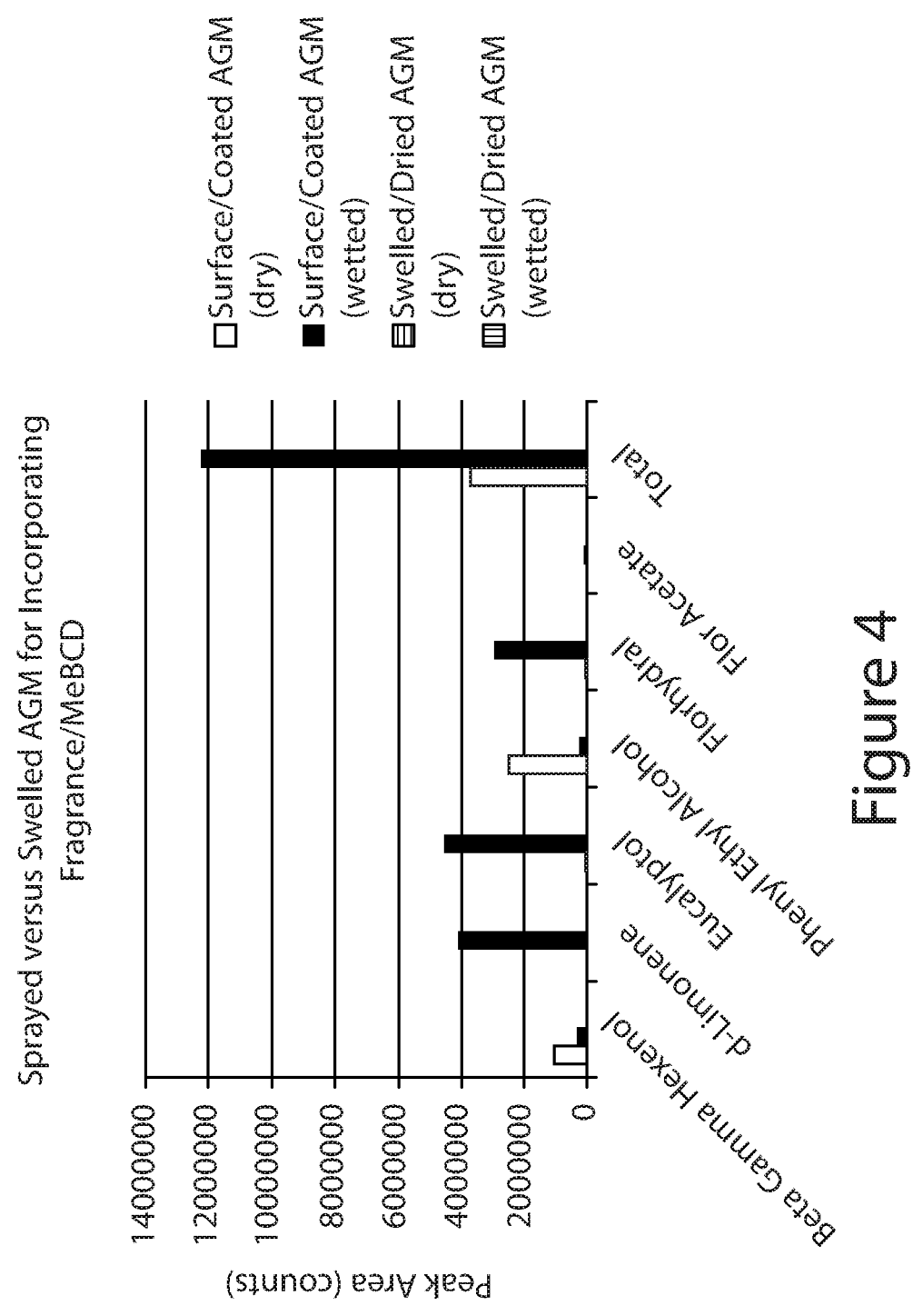

In FIG. 4, examples of swelled AGM versus dry AGM were compared regarding their perfume release. The graph of FIG. 4 shows the peak area of GC-MS signals for perfume materials release from MBCD encapsulated perfume incorporated into AGM (swelled AGM) versus MBCD encapsulated perfume coated onto AGM particles. MBCD was incorporated within AGM particles of some examples and coated on other examples.

As shown, examples where MBCD was incorporated into the AGM particle were found to exhibit negligible release of perfume materials upon wetting with water. In contrast, the AGM particles coated with MBCD released much more perfume than did the examples where MBCD was incorporated into the AGM. As shown, the perfume intensity may be much greater for the MBCD coated AGM particles when wetted versus the MBCD coated AGM particles when dry.

Figure 5:
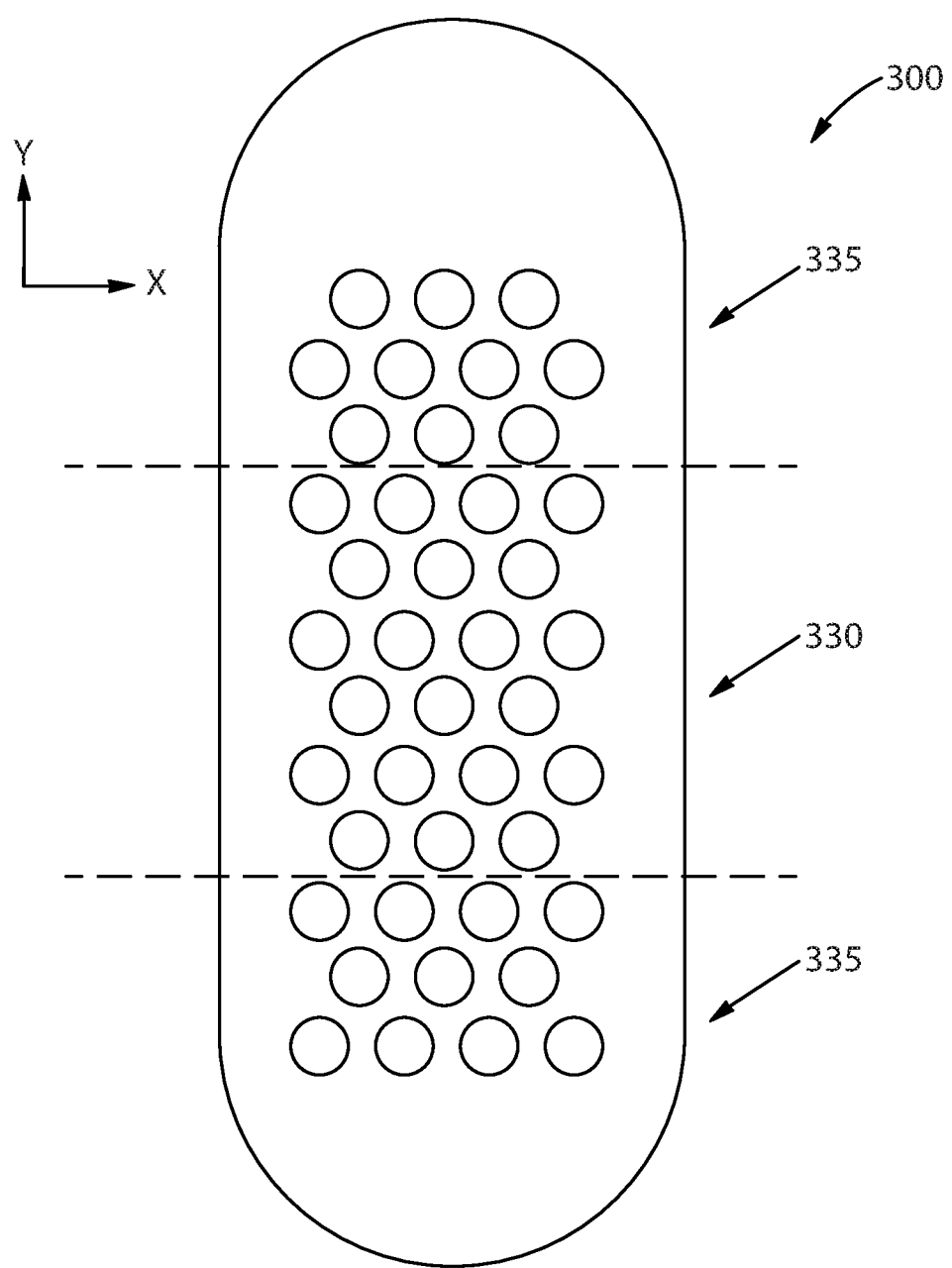
FIG. 5 is a schematic illustration of an absorbent article.

In some forms, the substituted cyclodextrin complex, e.g. MBCD, may be provided in a target zone of an absorbent article. As shown in FIG. 5, the target zone 330 of an absorbent article 300 represents the area of the absorbent article of expected fluid insult. The absorbent article 300 is shown having an overall longitudinal length generally parallel to a Y-axis and an overall lateral width generally parallel to an X-axis. The absorbent article 300 further comprises a thickness in a Z-direction (not shown) which is perpendicular to an X-Y plane created by the X and Y axes.

As shown, the target zone 330 may be disposed between two outer zones 335. In some forms, the target zone 330 may comprise about 60 percent of the overall longitudinal length (along a Y-axis) of the absorbent article 300 where each of the outer zones comprise about 30 percent or less of the overall length or less of the absorbent article 300. In some forms, the target zone 330 may comprise about 50 percent of the overall length while the outer zones 335 comprise about 40 percent or less of the overall length of the absorbent article. In some forms, the target zone 330 may extend from about more than 20 percent to less than about 80 percent, more than about 30 percent to less than about 70 percent, more than about 40 percent to less than about 60 percent of the overall length of the absorbent article 300, specifically including all values within these ranges and any ranges created thereby.

Forms are contemplated where the target zone 300 extends along only a portion of the overall lateral width (along an X-axis) of the absorbent article 300. For example, in some forms, the target zone 330 may extend for less than about 90 percent of the overall width of the absorbent article 300. As another example, the target zone 330 may extend for less than about 75 percent of the overall width of the absorbent article 300. Still in other forms, the target zone 330 may extend for less than about 50 percent of the overall width of the absorbent article 300. As yet another example, the target zone 330 may extend for about more than 10 percent to less than about 90 percent, more than about 20 percent to less than about 80 percent, more than about 30 percent to less than about 70 percent of the overall width, specifically including all values within these ranges and any ranges created thereby. In such forms, areas of the article outside of the target zone 330 may be sans the substituted cyclodextrin complex. Or in other forms, the target zone 330 may comprise more substituted cyclodextrin complex than either of the outer zones 335.

In the case of catamenial tampons the substituted cyclodextrin complex can be present on or in any component of the tampon, including the absorbent compressed pledget forming the tampon body, the overwrap, and the extraction cord. For example, it can be comprised in the tampon body, or on the tampon surface or, if an overwrap is present, on either surface of the overwrap. In case a secondary mass of absorbent material is present along the extension cord proximal to the extraction end of the tampon, the substituted cyclodextrin complex can be comprised within this secondary mass.

In all cases, the substituted cyclodextrin complex of the invention can be applied on one of the layers making up the absorbent article in powder form or can be incorporated into a liquid or semi-solid carrier and applied as a lotion. In this case, the substituted cyclodextrin complexes can be dispersed in a carrier to form a dispersion, and the dispersion applied to the absorbent article. The carrier can be selected for example from the group consisting of polysiloxane oil, mineral oil, petrolatum, polyethylene glycol, glycerin and the like, and mixtures thereof. The carrier is preferably polysiloxane oil, such as a silicone glycol copolymer (commercially available from Dow Corning as Dow Corning 190 Fluid).

The dispersion can be applied using conventional glue application equipment such as a slot applicator, which can be used for striped patterns, or air assisted applicators for patterned applications (like spray, spiral, serpentine, fibrils, Omega®, Signature® and the like). Patterned applications may allow one to position the complex in a way that it does not impact fluid acquisition (i.e. in a fem care article the material could not be applied in correspondence with the vaginal opening) and the pattern, having a large void space, allows fluid penetration also on the sides. Also, patterned applications are helpful because they allow a precise application so that it is easier to avoid contact with the glue which connects the various layers of the absorbent article.

However, for substituted cyclodextrin complexes of the present disclosure, another method of application to an absorbent article is available, which is not available for conventional cyclodextrin complexes. For substituted cyclodextrin complexes of the present disclosure, the complex may be formed directly in the site of the application. This is made possible by the fact that position-specific-substituted cyclodextrins, according to the invention, have an improved solubility both in water and in ethanol based solvents. This improved solubility allows one to prepare substituted cyclodextrin complexes of the present disclosure in the site of application (e.g. on a layer of material which is part of an absorbent article). And again, such method may not be applicable with unsubstituted cyclodextrins or completely substituted cyclodextrins, which each have lower solubility than position-specific-substituted cyclodextrins.

For the application method of substituted cyclodextrin complexes, the position-specific-substituted cyclodextrins may be solubilized in a solvent system. The solvent system may comprise at least 60%, at least 80%, or at least 95% of volatile solvents, specifically reciting all values within these ranges and any ranges created thereby. Some suitable examples of volatile solvents include water, C1-C8 alcohols, C1-C8 ketone and aldehydes, C1-C8 hydrocarbons, supercritical fluids, or even cooled gases in fluid form such as ethanol or mixtures thereof, together with the odor controlling organic compound forming a solution.

In some forms, the solvent system comprises less than 5%, less than 1.0%, or less than 0.5%, specifically reciting all values within these ranges and any ranges created thereby, of any non-volatile solvent(s) having a C Log P value less than 3. It is believed that such non-volatile solvents can interfere negatively with the crystallization of the CD complex.

In some forms, the viscosity of the solution is such that is easily pumpable or sprayable (if desired). For example, the viscosity may be less than 60 cp at 20° C. or less than 40 cp at 20° C., specifically reciting all values within these ranges and any ranges created thereby, (Brooksfield viscosity, measured at 20 $sec^{-1}$ and spindle 40 mm SST HB ST). Viscosity can be lowered by further diluting the solution. If solutions are prepared ahead of time prior to use, and water is used in combination with Ethanol, then the ratio of water to ethanol should be chosen to prevent the formation of microbial growth in storage. In some forms, the ratio of ethanol to water is at least 4/6 by weight.

In some forms, the odor controlling organic compound and the position-specific-substituted cyclodextrin are added to the solvent system mixture at a molar ratio of between 0.25:1 to 4:1, a molar ratio of between 0.5:1 to 2:1, or a molar ratio of between 0.8:1 to 1.2:1, specifically reciting all values within these ranges and any ranges created thereby. The resulting solution can be applied on any substrate making up the absorbent article with any type of applicator for liquid compositions e.g. with a drop applicator or a spray applicator. After application, upon evaporation of the volatile solvent, the complex is surprisingly formed in situ without the need of additional carriers for the application, surprisingly and the degree of complexing achieved is high.

It is believed that when the solvent which dissolves the cyclodextrin derivative evaporates, the cyclodextrin derivative can crystallize into a number of small microcrystals featuring different crystal shapes which do not stack thus allowing fluid to better penetrate and activate them when in use. Being formed in the presence of a fibrous substrate, the crystals tend to entrap some fibers and therefore to bind to it. This binding is advantageous because not only is loss of the odor controlling organic compound prevented but also positioning and dosing is facilitated as the complex forms and remains in the place where the solution is applied.

It is further believed that conventional cyclodextrin complexes stack into an ordered crystalline form—measurable by x-ray crystallography—which discourages liquid penetration into the crystalline form. In contrast, the substituted cyclodextrin complexes of the present disclosure are believed to form an amorphous crystalline structure which tends to be better suited for solubility.

Surprisingly, it has been discovered that by creating a di-substituted cyclodextrin composition, where in the substitution occurs predominantly in the 2 and 6 positions, the speed and completeness of release is dramatically increased of the odor control composition complexed in the cyclodextrin.

Without wishing to be bound by theory, it is believed that underivatized cyclodextrin cavities may hydrogen bond and stack into highly crystalline structures that prevent moisture from penetrating into the cavity and releasing the cavity contents. By replacing the hydroxyl groups on the top and bottom of the cavities (i.e. in the 2 and 6 positions), this prevents the cavities from stacking and leads to a more amorphous crystalline structure that can be more easily activated with moisture. Additionally, it is believed that as many of the hydroxyl groups in the 3 position as possible should be retained to promote water solubility. In some forms, the substituted cyclodextrin may have a dimethyl composition predominantly substituted in the 2 and 6 positions with a short chain hydrocarbon.

It may be important that during the manufacturing process, the volatile solvent evaporates as much as possible before the products are sealed into air tight plastic bags as it common for absorbent articles. Articles can be heated during manufacturing in order to facilitate the evaporation of the solvent, but this may not be necessary.

When the substituted cyclodextrin complex is introduced into the absorbent article as a coating on AGM particles, the coating can be obtained by depositing and evaporating a solution comprising the cyclodextrin and the one or more odor controlling organic compound as described above in the case of the application to any other layer or material of the absorbent article. Also, any other known coating method can be used.

More precisely coated AGM granules can be obtained, directly during the manufacturing operation of the absorbent article by spraying or otherwise depositing a solution comprising the cyclodextrin and the one or more odor controlling organic compounds dissolved in appropriate solvents as described above (e.g. ethanol, water, and mixtures thereof) onto the surface of the AGM in the assembly line before or after its application within the absorbent article (i.e. AGM can be treated with the substituted cyclodextrin complex solution when still in the drum, before application to the absorbent article or after having been deposited onto the absorbent article.

Alternatively, pre-coated AGM granules can be directly prepared in advance, e.g. directly by the AGM supplier and directly dosed in the manufacturing of the absorbent article, with the additional advantage of not having to control the evaporation of the solvent during the manufacturing of the article, especially in case article is manufactured at high speeds and then packaged in air tight packages as it is the case for certain absorbent articles.

Any suitable method of coating or application to the outside surface is appropriate. One method is to spray or mist a solution of the dissolved cyclodextrin, odor controlling organic compound(s) and appropriate solvents as described above onto the dry AGM particle surface (in this case it may be advantageous if the moisture of the dry AGM particle is less than about 20% moisture, preferably less than 10% moisture). Another method is to coat the AGM particle using the same solution and equipment such as a Wurster spray coater, commonly used to apply coatings to the outside surface of particles. Another method is to spray a solution on to a moving bed of dry AGM particles using a mist or spray applicator capable of creating a droplet size less than about half the size of AGM particle. Alternatively, effective coating of AGM particles can also be obtained by rapidly dipping a bed of AGM particles into a tank of a solution of the dissolved cyclodextrin, odor controlling organic compound(s) and appropriate solvents as described above, and remove it immediately thereafter to coat the outside surface without swelling the AGM particle is another method of coating the AGM particles. In all cases an appropriate drying step should follow using techniques which are common in the art. This said, forming coating on solid particles is a known process so that a skilled person would have many methods available in the common knowledge to achieve effective coating of the particles, as long as a method does not require the AGM particles to be in a prolonged contact with a large amount of water or other fluids which would swell the particle, that coating method would be suitable for obtained coated AGM particles according to the invention. Suitable methods are discussed in additional detail in U.S. Patent Application Publication No. 62/405,470.

Generally, it is preferred to apply a coating that results in a perfume to AGM weight ratio of between 1:100,000 to 1:1000 specifically reciting all values within these ranges and any ranges created thereby.

The one or more odor controlling compounds is typically comprised into an absorbent article in an amount of from about 0.01 to about 1000 milligrams per absorbent article, from about 0.1 to about 100 milligrams per absorbent article, or from about 0.1 to about 500 milligrams per absorbent article, specifically reciting all values within these ranges and any ranges created thereby.

The recited milligrams per absorbent article are applicable in general to any absorbent article, however absorbent articles can have very different sizes and therefore may contain more or less of the one or more odor controlling compounds, depending on need. Because of the effectiveness of the odor control technology of the present disclosure, a lower level of odor controlling compounds can be used to achieve effective odor control versus conventional odor control technologies as shown in Table 3 below.

For example, considering absorbent articles for personal hygiene the typical amounts are shown in Table 3 (the weight indicated only refers to the one or more odor controlling compound and excludes to the cyclodextrin used to for the complex with it):

TABLE 3

| Absorbent article | Range (in mg) | |
|---|---|---|
| | Min | Max |
| Panty-Liners | 0.1 | 5 |
| Sanitary Napkins | 0.2 | 20 |
| Adult incontinence pads | 0.5 | 30 |
| Adult incontinence Diapers | 1 | 50 |
| Baby Diapers | 1 | 50 |
| Tissue paper (roll) | 0.2 | 20 |

In some forms of the present invention, a substituted cyclodextrin complex may comprise the one or more odor controlling compounds which are provided in an absorbent article at the above levels. However, as discussed heretofore, substituted cyclodextrin complexes may have higher solubility than conventional cyclodextrin complexes. As such, a lower amount of the one or more odor controlling compounds may be utilized and still deliver an effective amount of fragrance. Accordingly, forms of the present invention are contemplated where the one or more odor controlling compounds are provided in a substituted cyclodextrin and is provided at less than about 90 percent of the levels of Table 3, at less than about 75 percent of the levels of Table 3, at less than about 60 percent of the levels of Table 3, at less than about 50 percent of the levels of Table 3, at less than about 35 percent of the levels of Table 3, at less than about 25 percent of the levels of Table 3, greater than about 10 percent of the levels of Table 3, specifically including all values within these ranges and any ranges created thereby.

Any of the known odor controlling organic compound which form stable complexes with cyclodextrin can be used in the present invention, only one odor controlling organic compound can be used or more odor controlling organic compounds can be used in combination. Examples of suitable odor controlling organic compounds are mentioned here below in lists (a/a*), (b), (c), (d), and (e). It is in general preferred that at least one reactive compound from lists (a/a*) or (b) is present.

List a) includes reactive compounds having a "thiol vapor pressure suppression index" (TVPS) of more than 20.

Thiol Vapor Pressure Suppression (TVPS) index is a measure of the reduction in butanethiol concentration in the headspace by a compound, as measured using a fast GC instrument, the zNose 7100 (Electronic Sensor Technologies, Newbury Park, Calif.).

Examples of preferred reactive compounds which are suitable for the present invention and which have a TVPS higher than 20 are those of the following list (a*), these compounds not only have a TVPS higher than 20 but they also form complexes with cyclodextrin which are particularly stable and release the complexed materials when needed.

(a*): melonal, adoxal, trans-2-hexenal, ligustral, Floral Super, Florhydral, 5-methyl-2-thiophene-carboxaldehyde, hydratropic aldehyde, undecenal, 9-undecenal, 10-undecenal, trans-4-decenal, cis-6-nonenal, isocyclocitral, precyclemone b, (E)-2,(z)-6-nonadienal, undecyl aldehyde, methyl-octyl-acetaldehyde, Lauric aldehyde, silvial, vanillin, floralozone.

All these compounds in list (a/a*) are particularly reactive toward malodorant molecules containing Sulfur atoms (thiol type malodors, typically associated with protein degradation e.g. in menstrual fluids, feces, food etc).

Additional reactive aldehydes and/or ketones which can be advantageously used include the following listed in list (b): hexyl cinnamic aldehyde, alpha-amylcinnamic aldehyde, p-anisaldehyde, benzaldehyde, cinnamic aldehyde, cuminic aldehyde, decanal, cyclamen aldehyde, p-t-butyl-alpha-methyldihydrocinnamaldehyde, 4-hydroxy-3-methoxycinnamaldehyde, vanillin isobutyrate, 2-phenyl-3-(2-furyl)prop-2-enal, ethyl vanillin acetate, vanillin acetate, heptanal, lauryl aldehyde, nonanal, octanal, phenylacetaldehyde, phenyl propyl aldehyde, salycil aldehyde, citral, 2,4-dihydroxy-3-methylbenzaldehyde, 2-hydroxy-4-methylbenzaldehyde, 5-methyl salicylic aldehydes, 4-nitrobenzaldehyde, o-nitrobenzaldehyde, 5-ethyl-2-thiophenecarbaldehyde, 2-thiophenecarbaldehyde, asaronaldehyde, 5-(hydroxymethyl)-2-furaldehyde, 2-benzofurancarboxaldehyde, 2,3,4-trimethoxybenzaldehyde, protocatechualdehyde, heliotropine, 4-ethoxy-3-methoxy benzaldehyde, 3,4,5-trimethoxybenzaldehyde, 3-hydroxybenzaldehyde, o-methoxycinnamaldehyde, 3,5-dimethoxy-4-hydroxycinnamaldehyde, 2,8-dithianon-4-3n-4-carboxaldehyde, sorbinaldehyde, 2,4-heptadienal, 2,4-decadienal, 2,4-nonadienal, 2,4-nonadienal, (E,E)-,2,4-octadien-1-al, 2,4-octadienal, 2,4-dodecadienal, 2,4-undecadienal, 2,4-tridecadien-1-al, 2-trans-4-cis-7-cis-tridecatrienal, pieronylidene propionaldehyde, 2-methyl-3-(2-furyl)acrolein, 2,4-pentadienal, 2-furfurylidene butyrraldehyde, helional, lyral, 3-hexenal, safranal, veratraldehyde, 3-(2-furyl)acrolein, pyruvaldehyde, ethanedial, 1-(2,6,6-trimethyl-1-cyclohexenyl)pent-1-en-3-one; 4-(2,6,6-trimethyl-1-cyclohexen-1-yl)-3-Buten-2-one; 4-(2,6,6-trimethyl-2-cyclohexen-1-yl)-3-buten-2-one, 5-(2,6,6-Trimethyl-2-cyclohexen-1-yl)4-penten-3-one, (E)-4-(2,2-dimethyl-6-methylidenecyclohexyl)but-3-en-2-one.

Compounds in list (b) are aldehydes and/or ketones which are able to react with some classes of malodorant compounds, in particular nitrogen based malodorant compounds, and do not have unpleasant odor.

Reactive compounds in lists (a/a*) and (b) chemically react with malodors, such as malodorant molecules containing Nitrogen atoms (amine type odors, typically deriving from the degradation of urine or certain foods like onions) and/or malodorant molecules containing Sulfur atoms (thiol type malodors, typically associated with protein degradation e.g. in menstrual fluids, feces, food etc). Ammonia/amines are one component of malodor associated with the absorption of bodily fluids, such as menses or urine. For example, ammonia/amines are typically present in high amounts in absorbent products used for urine absorption due to degradation of urea. Ammonia/amines and their derivatives can react with aldehydes and/or ketones to form imines (according to the so-called Schiff base reaction).

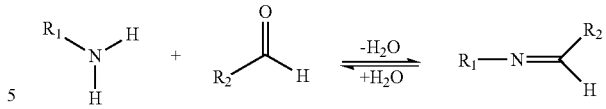

This reaction is catalyzed by enzymes and/or by a slightly acidic pH 4 to 5. The moderate acid requirement is necessary to allow protonation of the hydroxyl intermediate to allow water to leave.

Malodorant sulfur based compounds are typically generated by the degradation of proteins e.g. in menstrual fluids feces or food and so their control is particularly important in menstrual absorbent articles such as sanitary napkins or pantyliners as well as in other absorbent articles which get in contact with other proteinaceous materials such food residues or feces. The mechanism of action is not fully understood at the moment, but it is believed that it is connected to the fact that Thiols can react with aldehydes and ketones to form thioacetals and tioketals.

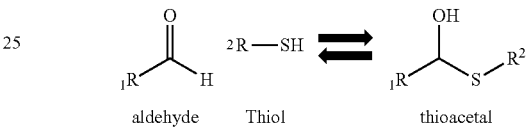

In principle, the chemical reactions described above can be obtained from any aldehyde, but in practice the reactivity of aldehydes in these type of reactions and in the specific context of an absorbent article is very different. The reactive compounds (a) and (b) of the present invention are effective in reacting with Nitrogen based malodorant molecules and those according to (a) are particularly effective in reacting also with sulfur based malodorant molecules.

The particularly high reactivity of these reactive compounds towards sulfur based malodorant molecules renders them effective for use in absorbent articles which are used to absorb menses.

The preferred reactive compounds of the present invention are particularly advantageous in the specific context of absorbent articles because they have a pleasant and low intensity odor and are also able to be complexed effectively and to be quickly released when needed.

Another important aspect of the present invention is that each complexed reactive compound has an individual character in terms of odor. Therefore, their introduction within an absorbent article also represents the possibility to provide not only reactivity on malodors but also individual fragrant notes which can be combined with other odorous components (encapsulated/complexed and/or in free uncomplexed form) thus allowing the formulator to obtain a broader range of fragrances being released by the product when used i.e. when the complexed reactive compound is activated.

Other odor controlling organic compounds which can be used herein include particular other fragrance/masking/reacting components selected from the lists (c), (d) and (e). Components from list (c) are menthol, menthyl acetate, menthyl lactate, menthyl propionate, menthyl butyrrate, menthone, mint terpenes, laevo-carvone, Cis-3-Hexenol & Cis-3-Hexenyl acetate, koavone, methyl dioxolan, ethylene brassylate, and salycilate esters. Salycilate esters are preferably selected from amyl salicylate, isoamyl salicylate, isobutyl salicylate, cis-3-hexenyl salicylate, hexyl salicylate, cyclohexyl salicylate, benzyl salicylate, phenylethyl salicylate, propyl salicylate, isopropyl salicylate or mixtures thereof.

These are all compounds which primary function is to mask malodors. This may occur through vapor pressure suppression of the malodor or by overwhelming the unpleasant malodor with the pleasant odor of the fragrance component. These materials, when used, may significantly reduce the ability to detect the malodors. The masking ability to hide malodors is possible due to the volatile nature of the materials selected, which are released from the complex in the absorbent article and are then inhaled into the nose of a consumer, generally within somewhat close range of the absorbent article, e.g. within about 0 to 10 meters of the article by normal breathing (although this should in no way be intended to limit the scope of the invention).

Components from list (d) are methyl-dihydrojasmonate, methyl jasmonate, eucalyptol, tetrahydro-linalool, phenylethyl alcohol, hexyl iso-butyrate, linalyl acetate, benzyl acetate, Benzyl alcohol, or mixture thereof. These are volatile materials which are well complexed with cyclodextrin and are released very quickly upon contact with a water based liquid. Their presence allows the absorbent article to respond even more quickly to an insult of malodorant liquid by releasing a compound that have a good general masking effect against malodors, in particular, being very volatile, reduces the vapor pressure of other malodorant compounds slowing down their evaporation rate.

List (e) includes other malodor masking and fragrance components which can be used s odor controlling organic compounds in the present invention:

e) camphor, p-menthane, limonene, cresol, linalool, myrcenol, tetra hydromyrcenol, di-hydromyrcenol, myrcene, citronellol, citronellyil derivatives, geraniol, geranyl derivatives, mugetanol, eugenol, jasmal, terpineol, pinanol, cedrene, damascone, beta pinene, cineole and its derivatives, nonadienol, ethylhexanal, octanol acetate, methyl furfural, terpinene, thujene, amylacetate, camphene, citronellal, hydroxycitronellal, ethyl maltol, methyl phenyl carbinyl acetate, dihydrocumarin, di-hydromyrcenyl acetate, geraniol, geranial, isoamylacetate, ethyl, and/or triethyl acetate, para-cresol, para-cymene, methyl abietate, hexyl-2-methyl butyrate, hexyl-2-methyl butyrate, and mixtures thereof.

All the compounds mentioned within the present application, unless a specific isomeric form is specified, also include their isomeric forms, diastereomers and enantiomers.

It may be that, for certain components, the same component can be considered both a malodor reactive component, a malodor masking component, and/or a fragrance component.

In embodiments of the invention wherein one or more odor controlling organic compounds from the lists above are present the complex can be prepared mixing all compounds together before preparing the complex, or, alternatively, substituted cyclodextrin complexes containing only one or only some of the compounds can be prepared separately and then mixed according to the desires dosages before introduction into the absorbent article.

In some embodiments, the absorbent articles of the present invention, in addition to the components from lists a), b), c), d) and e) in complexed form may also include components from the same lists or other fragrance components in free form or in encapsulated form.

In the present invention, it is however preferred that the absorbent article exhibits no noticeable scent (or very little scent) before use. As a result, it is preferred that no or a small level of other fragrant compounds are present and that the complexed compounds are complexed efficiently and completely so that only a low amount of free components are present before product usage and are released only during the utilization of the absorbent article.

The present invention further encompasses a method of reducing malodor associated with malodorant fluids e.g. bodily fluid such as urine, menses, and/or feces, comprising the step of contacting the fluid with an absorbent article of the present invention. Preferably, the method reduces the malodor associated with the malodorant fluids.

The present invention also encompasses a method of making an absorbent article which comprises the step of applying onto one of the materials making up the article the cyclodextrin complexes according to the present invention.

Test Procedures

Thiol Vapor Pressure Suppression Index (TVPS) Measurement

Thiol Vapor Pressure Suppression (TVPS) index is a measure of the reduction in butanethiol concentration in the headspace by a compound, as measured using a fast GC instrument, the zNose 7100 (Electronic Sensor Technologies, Newbury Park, Calif.) based on an Surface Acoustic Wave (SAW) Quartz microbalance detector, or equivalent.

Before any measurements the instrument is calibrated according to manufacturer's instructions under the same experimental settings. The instrument has a DB-5 column (also available from Electronic Sensor Technologies, Newbury Park, Calif.) 1 m in length, 0.25 µm phase thickness, and 0.25 mm in diameter.

For analysis, the zNose is programmed with the Sensor Temperature, Inlet Temperature, Valve Temperature, and Initial Column Temperature all set to 40° C. The oven is temperature gradient is programmed at a rate of 10 C°/s from 40° C. to a final temperature of 200° C.

TVPS of a compound is measured in the following way: 100 µl±1 µl of a 1% v/v butanethiol (99%, purity, available from Sigma-Aldrich, St. Louis, Mo.) solution in ethanol (200 proof) is added into a 1 ml vial (8×40 mm). These vials are borosilcate glass straight walled vial. In another 1 ml vial (8×40 mm), 5 µl±0.2 µl of the compound is added. Both open vials are then placed inside a 20 mL headspace vial (22×75 mm), and the vial is immediately sealed using a screw thread closure with PTFE/Silicone septa. The vial is heated to 37° C. for 4 hours. After 4 hours, the vial is removed from the oven and let to equilibrate at 25° C.±2° C. for 15 minutes. The headspace inside the vial is sampled using the zNose is sampled for 10 s and analyzed following the experimental protocol outlined above. Samples with butanethiol alone, and the volatile active alone, are run using the same protocol to identify the peaks for both materials. An acceptable retention index for butanethiol is 720±30. If the peaks butanethiol peak and the volatile material peak co-elute, one skilled in the art can modify the protocol settings to separate those peaks to achieve a minimum resolution of 1.5. For example one can change the column temperature ramp rate. In between samples, the instrument needs to be cleaned to remove any trace materials. To clean the instrument, the instrument is run without samples as needed until no peaks greater than 100 counts are observed.

The amount of butanethiol in the headspace is measured from the area of the peak on the chromatograph for butanethiol ($A_{BtSH,Rx}$). To calculate the percentage of butanethiol reduction in the headspace, a control with the butanethiol solution without the volatile material is run in the same manner and the area is measured as well ($A_{BtSH,C}$). TVPS is then measured as the percentage reduction in butanethiol area calculated using the following formula:

$$TVPS = \frac{A_{BtSH,C} - A_{BtSH,Rx}}{A_{BtSH,C}} \times 100$$

An example of the type of measurements obtained with the instrument is:

| Sample | Butanethiol Peak Retention Index | Area (counts) |
|---|---|---|
| Butanethiol Control Vial 1: 100 µl of 1% v/v butanethiol in ethanol Vial 2: Empty | 720 | $A_{BtSH, C}$ = 4934 |
| Butanethiol + Florhydral Vial 1: 100 µl of 1% v/v butanethiol in ethanol Vial 2: 5 µl Florhydral | 720 | $A_{BtSH, Rx}$ = 2442 |

Example TVPS calculation for $$TVPS = \frac{4934 - 2442}{4934} \times 100 = 50.5\%$$

The value of TVPS for several compounds suitable for the invention is presented in the table below. TVPS for the compounds indicated with (*) have been approximated using a mathematical model calculated starting from real measurements on a large number of compounds. The model is created using the QSAR software CAChe ProjectLeader WorkSystem Pro 7.1. Using the molecular structure from the compounds for which TVPS was evaluated, several molecular properties are calculated. A regression algorithm is the used to calculate the best fit to predict TVPS based on the 4 molecular descriptors that best fit the data. The model is then used to predict TVPS for other compounds using the same software. The values of TVPS approximated with the molecular modeling system are presented for illustration only, for the avoidance of doubt it is specified that the TVPS values for use in the present inventions are only the TVPS values measured with the zNose analytical method described above.

| | TVPS |
|---|---|
| melonal | 20.4 |
| adoxal | 24.4 |
| trans-2-hexenal | 27.1 |
| ligustral | 42.5 |
| Floral Super | 52.4 |
| Florhydral | 53.3 |
| 5-methyl-2-thiophene-carboxaldehyde | 67.4 |
| hydratropic aldehyde(*) | 72.0 |
| Undecenal(*) | 26.2 |
| 9-undecenal(*) | 67.5 |
| 10-undecenal(*) | 52.0 |
| trans-4-decenal(*) | 60.3 |
| cis-6-nonenal(*) | 57.1 |
| isocyclocitral(*) | 51.4 |
| precyclemone b(*) | 40.7 |
| (E)-2-(z)-6-nonadienal(*) | 35.8 |
| undecyl aldehyde(*) | 34.9 |
| methyl-octyl-acetaldehyde(*) | 30.2 |
| Lauric aldehyde(*) | 26.6 |
| silvial(*) | 25.8 |
| vanillin(*) | 23.7 |
| floralozone(*) | 23.5 |
| Hexylcinnamic aldehyde | 8.0 |
| neral | 17.1 |
| ethyl vanillin | 2.9 |

Comparison of Fragrance Release of Different Methyl Substituted β-Cyclodextrin

Figure 2:
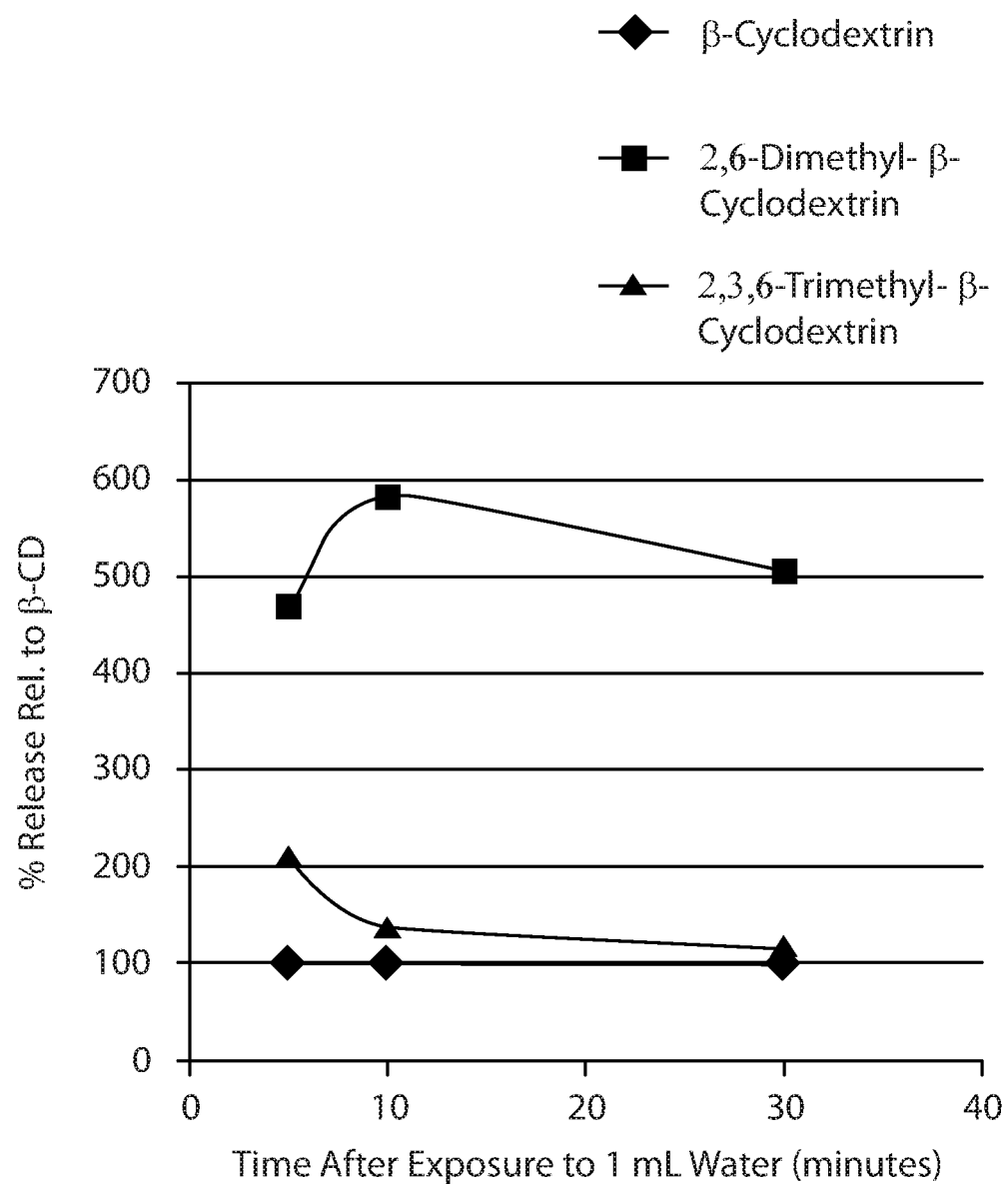
FIG. 2 is a graph depicting the release effectiveness among several cyclodextrin complexes.

To demonstrate the perfume release effectiveness of different methyl substituted, β-Cyclodextrin (available from TCI America, OR, or equivalent), 2,6-Di-O-methyl-β-cyclodextrin (available from Acros Organics, NJ or equivalent), and 2,3,6-Tri-O-methyl-β-cyclodextrin (available from TCI America, or equivalent) were each complexed with a model blend of Odor Controlling Organic Compounds (indicated with the acronym OCOC) and spiked onto a portion of an ultra, feminine hygiene pad (a suitable pad is Always Ultra by Procter and Gamble, or equivalent). The results are shown in the graph of FIG. 2. After dosing with water the headspace was sampled using Solid Phase Micro-Extraction (a suitable fiber assembly is a 2 cm Stableflex 24 Ga, 50/30 µm DVB/CAR/PDMS available from Supelco, Pa. or equivalent) followed by gas chromatography/mass spectrometry (a suitable unit is the 5777A Mass Selective Detector (MSD) also available from Agilent, or equivalent) with a GERSTEL Multipurpose Sampler (Gerstel, Liticumo, Md. or equivalent) to quantify the OCOC release.

The model OCOC used is a neat mixture of benzaldehyde (1.6 g, 15.08 mmols), ligustral (1.6 g, 11.58 mmols), citral (1.6 g, 10.51 mmols), cinnamic aldehyde (1.6 g, 12.11 mmols), and florhydral (1.6 g, 8.41 mmols). All components are available from Sigma Aldrich, or equivalent. The mixture is homogenized before use.

The Standard Pad Substrates are prepared by cutting a 10 cm lateral strip across the whole product centered at the longitudinal center of an Always Ultra normal size pad.

A mixture of the model OCOC for each β-cyclodextrin type was solubilized in water at a one-to-one molar ratio (β-cyclodextrin/OCOC). The amount of water used for the complexation was adjusted for each β-cyclodextrin type according to its individual water solubility to ensure complete dissolution of the β-cyclodextrin complex. Each mixture of β-cyclodextrin and OCOC in water was thoroughly homogenized. Solutions of β-cyclodextrin, OCOC, and water were dosed onto a Pad Substrate. An amount of solution was added to each pad such that an equivalent of 1 mg of OCOC (complexed by β-cyclodextrin) is available for release upon addition of water. Pads dosed with the above described solution were exposed to open air at room temperature for four days to allow water to evaporate leaving only perfume complexed by β-cyclodextrin. Specifically:

Add 555 mg β-cyclodextrin and 68 mg model OCOC to 30 mL of purified water and mixed thoroughly. 810 µL of this solution (adjusted for losses due to evaporation) is dosed at the longitudinal and lateral center of the pad substrate.

Add 2011 mg 2,6-di-O-methyl-β-cyclodextrin (38.4%) and 210 mg model OCOC (4%) to 3 mL of purified water and mixed thoroughly. 16 µL of this solution (adjusted for losses due to evaporation) was added to the longitudinal and lateral center of the pad substrate.

Add 1008 mg 2,3,6-tri-O-methyl-β-cyclodextrin (4.8%) and 98 mg model OCOC (0.46%) to 20 mL of purified water and mixed thoroughly. 452 µL of this solution (adjusted for losses due to evaporation) is dosed at the longitudinal and lateral center of the pad substrate.

The control is prepared by dosing 1.0 mg of the neat OCOC at the longitudinal and lateral center of the pad substrate. The control is prepared immediately before dosing with the water The GC analysis was performed on a 30 m long by 0.250 mm diameter column with 5% phenyl arylene methylpolysiloxane phase at a 1 μm film thickness (a suitable column is the DBSMS available from Agilent, or equivalent USP G27 phase). The GC inlet was set at 280° C. in Split-less mode (A CIS-4 SPME low volume glass linear available from Sigma-Aldrich) with a 3 mL septum purge. A 1.5 mL column flow of helium was set at an oven temperature of 150° C. under constant flow conditions. The GC oven was programmed to begin at 150° C. for 1 min, then ramp at 16° C./min to 230° C., hold for 6 min at 230° C., then ramp at 30° C./min to 300° C. and a final hold of 1 min Upon injection, the SPME fiber is left in the injector for 5.00 min.

The temperature for the MSD transfer line and detector were set to 280° C. and 300° C. respectively. The MSD was configured for electron ionization at −70 eV scanning from 35 m/z to 300 m/z with a scan rate of 192 msec/scan. A Total Ion Chromatogram (TIC) is collected for each specimen. The TIC is then processed to extract ion chromatograms at 106 m/z (benzaldehyde), 67 m/z (ligustral) 69 m/z (citral), 131 m/z (cinnamic aldehyde) and 105 m/z (forhydral). The peaks of interest in the extracted ion chromatogram are integrated and summed.

Each absorbent article Specimens was placed in a 250 mL glass jar and sealed with a PTFE/silicone septum lid (fluoropolymer resin-lined, available from I-CHEM, Thermo Scientific, or equivalent). The pad is positioned along the wall of the jar with the back sheet against the wall. The jar is placed on its side and rotated such that the longitudinal center of the substrate can be dosed with 1.00 mL of purified water. The jar is sealed and the headspace sampled using the SPME for 30 sec at 5, 10, and 30 minute time points after the addition of water. The control is analyzed in like fashion for comparison.

The % Release is based on the summed area of the peaks of interest within the extracted ion chromatogram, normalized to the applied mass of the cyclodextrin: % Release= (Summed Area Counts of β-cyclodextrin/Summed Area counts of control)/mg of β-cyclodextrin dosed on pad In like fashion, three replicates of each β-cyclodextrin complex and control are analyzed and the % Release is calculated for each. The % Release is reported as the arithmetic mean of the three replicates to the nearest 0.1%/mg. Results are graphed in FIG. 2 showing perfume release from pads per mg dimethyl- and trimethyl-β-cylclodextrin versus underivatized β-cyclodextrin.

As shown in the graph of FIG. 2, the inventors have surprisingly found that 2,6-dimethyl-β-cyclodextrin provides a much higher percent release of fragrance than does conventional β-cyclodextrin. Similarly, 2,6-dimethyl-β-cyclodextrin also provides a much higher release of fragrance than does 2, 3, 6-trimethyl-β-cyclodextrin. As shown, in some forms, the substituted cyclodextrin complexes of the present invention may provide a percent fragrance release of greater than about 200 percent of that of conventional β-cyclodextrin after 10 minutes. In some forms, the substituted cyclodextrin complexes of the present invention may provide a percent fragrance release of greater than about 300 percent of that of conventional β-cyclodextrin after 10 minutes, greater than about 400 percent after 10 minutes, greater than about 500 percent after 10 minutes, greater than about 500 percent after 20 minutes, or greater than about 500 percent after 30 minutes, specifically reciting all values within these ranges and any ranges created thereby.

Effectiveness of Location of Substituted Cyclodextrin Complex

The effectiveness of the MBCD complex within an absorbent article was analyzed by headspace solid-phase microextraction (SPME) followed by gas chromatography/mass spectrometry.

The GC analysis was performed on a 30 m long by 0.250 mm diameter column with 5% phenyl arylene methylpolysiloxane phase at a 1 μm film thickness (a suitable column is the DBSMS available from Agilent, or equivalent USP G27 phase). The GC inlet was set at 280° C. in Split-less mode (A CIS-4 SPME low volume glass linear available from Sigma-Aldrich) with a 3 mL septum purge. A 1.5 mL column flow of helium was set at an oven temperature of 60° C. under constant flow conditions. The GC oven was programmed to begin at 60° C. for 1 min, then ramp at 10° C./min to 215° C., then ramp at 25° C./min to 315° C. and a final hold of 2.5 min. A 24 gauge SPME fiber assembly (50/30 μm DVB/CAR/PDMS, Stableflex 2 cm fiber) is used to collect headspace. Upon injection, the SPME fiber is left in the injector for 1 min followed by a 1.0 min post extraction of the headspace above an external standard solution consisting of ethyl linalool solubilized in 3 mL of a 12% sodium dodecyl sulfate solution at a concentration of 1000 parts per million (ppm).

The temperature for the MSD transfer line and detector were set to 230° C. and 40° C. respectively. The MSD was configured for electron ionization at −70 eV scanning from 35 m/z to 400 m/z with a scan rate of 1424 amu/sec and a minimum threshold signal of 250 counts. A Total Ion Chromatogram (TIC) is collected for each specimen. Analyte signal areas are ratioed to the peak area of the external standard.

A specimen is collected as die cut a circular 4 cm diameter (12.57 cm$^2$) specimen from the article at the region of interest, e.g. target zone described heretofore. The specimen contains all layers of the article. The specimen can be measure intact or sub-sectioned in the z-direction (see FIG. 5) into individual layers. Each specimen was placed in a 125 mL specimen jar (e.g. EPA Clear Wide-Mouth Septa Jars, VWR part # UX-99540-21, with PTFE-lined Silicone septum, VWR part #1BT58-400W0T, or equivalent). 3.0 mL of Millipore purified water, is added to a specimen and the jar is sealed for 4.0 hours at room 23° C. before sampling. Relative fragrance intensity differences between each unique sample were measured via SPME-GC/MS as described above.

As an illustration of MBCD/perfume presence on different layers of an article, a Pampers Swaddler diaper (Article A) was made in parallel to a diaper identical with the exception that no SAP was added to the core (Article B).

A test perfume consisting of beta gamma hexenol (CAS#928-96-1), d-limonene (CAS#5989-27-5), eucalyptol (CAS#470-82-6), phenyl ethyl alcohol (60-12-8), florhydral (CAS#125109-85-5), and flor acetate (CAS#5413-60-5) is prepared. The MBCD/perfume dose solution is a mixture of Millipore purified water (2 g, 28.4 wt. %), ethanol (2 g, 28.4 wt. %), methylated β-cyclodextrin (CAVASOL® W7 M from Wacker Chemie AG, 2.67 g, 37.8 wt. %), and perfume, (381 mg, 5.4 wt. %). MBCD solutions are nebulized using an X-175 Nebulizer (175 μm capillary) (Burgener Research, Mississauga, Ontario, Canada, or equivalent), with a 40 PSI nitrogen back pressure. The solutions are introduced into the nebulizer at a specified flow rate using a syringe pump (e.g. Cole-Parmer 74900 series single-syringe infusion pump, or equivalent).

MBCD/perfume treated SAP was prepared by nebulization of the MBCD/perfume onto the SAP and by swelling the SAP with an aqueous MBCD/perfume mixture.

Nebulization on SAP: 10 g of particulate SAP (available from Nippon Shokubai) was distributed evenly over the bottom of a 100 mm diameter glass petri dish. 20 µL of the MBCD/perfume dose solution (approximately 1.1 mg perfume) was nebulized uniformly over the surface of the SAP. The nebulizer was held approximately 8 cm above the SAP and mixture was deposited at 20 µL min$^{-1}$ for 1.0 min Spray-coated AGM was dried at room temperature for 15 min then transferred to a 40 mL glass vial, capped, and shaken vigorously by hand for 30 seconds to thoroughly mix the SAP particles.

Swelling of SAP: 10 g of particulate SAP (available from Nippon Shokubai) is placed into a 500 mL glass beaker. 20 µL of the MBCD/perfume dose solution (approximately 1.1 mg perfume) is added to 75 mL of Millipore purified water and mixed thoroughly. All 75 mL is added to the beaker and the SAP is allowed to completely absorb the mixture. The swelled material was distributed evenly within a 190×100 mm glass petri dish and placed in an oven at 100° C. for 2 hours to dry.

Article A is prepared by die cutting a circular 4 cm diameter (12.57 cm2) specimen from the article at the longitudinal and lateral center of the article. The specimen contains all layers of the article. Five specimens are prepared for each layer to be tested. For the topsheet, the nebulizer was positioned 4 cm above the center of the specimen. The specimen was rotated at a rate of 100 to 200 rpm as 0.9 µL of the MBCD/perfume dose solution was nebulized onto the surface at a rate of 10 µL min$^{-1}$. Specimen is set out on the benchtop and allowed to dry for 15 minutes at room temperature before placing into a 125 mL specimen jar (e.g. EPA Clear Wide-Mouth Septa Jars, VWR part # UX-99540-21, or equivalent).

Specimens from additional Article A samples are prepared dosing other layers from the article, for this example the Acquisition Layer (AQL) and the non-woven core cover (NWCC). For the AQL, the top sheet is removed from the specimen and set aside. The surface of the AQL is then dosed in like fashion to the top sheet. After drying for 15 minutes the top sheet is replaced before sealing it into a specimen jar. The same procedure is repeated for the NWCC.

To evaluate the effectiveness of MBCD deposited on SAP, die cut a circular 4 cm diameter (12.57 cm2) specimen from the article at the longitudinal and lateral center of Article B. Remove all layers above the NWCC and place 472 mg of the spray coated SAP prepared above. Replace the upper layers of the specimen and place into a 125 mL specimen jar.

Specimens are then analyzed using the SPME/GC/MS method as described above.

Extraction of Mbcd from Absorbent Articles

MBCD can be collected from whole articles or components by Soxhlet extraction with water and the subsequent removal of solvent (water) using a rotary-evaporator. For further analysis of methyl substitution, enough articles need to be extracted to collect 50 mg of MBCD.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a substituted cyclodextrin complex of one or more odor controlling organic compounds wherein said substituted cyclodextrin complex comprises cyclodextrin molecules which are substituted (wherein the H atom of OH groups in positions 2, 3 and 6 is partially or entirely replaced by a substituent —R), wherein the substituted cyclodextrin complex has a substitution degree (DS) of about 0.4 to about 2.5 —R substituents per glucose unit of cyclodextrin and wherein substitution in position 2 is 20% or above, in position 6 is 20% or above and substitution in position 3 is less than that of position 2 and/or position 6.

2. An absorbent article according to claim 1 wherein the cyclodextrin has a substitution degree of from 0.9 to 2.4.

3. An absorbent article according to claim 1, wherein the substitution in position 2 is between about 20 percent to about 90 percent.

4. An absorbent article according to claim 1, wherein the substitution in position 2 is between about 45 percent to about 80 percent.

5. An absorbent article according to claim 1, wherein the substitution in position 6 is between about 20 percent to about 90 percent.

6. An absorbent article according to claim 2, wherein the substitution in position 6 is between about 40 percent to about 80 percent.

7. An absorbent article according to claim 1, wherein the R substituents are selected from linear or branched C1-C5 saturated chain.

8. An absorbent article according to claim 1, wherein the R substituents are selected, from methyl and hydroxymethyl and are preferably methyl.

9. An absorbent article according to claim 1, wherein the article comprises an absorbent core and wherein the cyclodextrin complex is provided on the absorbent core.

10. An absorbent article according to claim 1, wherein the substitution in position 3 is between about 10 percent to about 50 percent.

11. An absorbent article according to claim 1, wherein the substitution in position 3 is between about 20 percent and about 40 percent.

12. An absorbent article according to claim 10, wherein the substitution in position 2 is between about 20 percent to about 90 percent.

13. An absorbent article according to claim 10, wherein the substitution in position 2 is between about 45 percent to about 80 percent.

14. An absorbent article according to claim 10, wherein the substitution in position 6 is between about 20 percent to about 90 percent.

15. An absorbent article according to claim 10, wherein the substitution in position 6 is between about 40 percent to about 80 percent.

16. An absorbent article according to claim 10, wherein cyclodextrin has a substitution degree of from 1.6 to 2.1.

* * * * *